US012629003B2

(12) United States Patent
Magno et al.

(10) Patent No.: US 12,629,003 B2
(45) Date of Patent: May 19, 2026

(54) QUICK CONNECT SUB-ASSEMBLIES FOR SCOPES

(71) Applicant: OLYMPUS MEDICAL SYSTEMS CORP., Tokyo (JP)

(72) Inventors: Joey Magno, Dudley, MA (US); Yasuaki Kasai, Saitama (JP)

(73) Assignee: OLYMPUS MEDICAL SYSTEMS CORP, Tokyo (JP)

( * ) Notice: Subject to any disclaimer, the term of this patent is extended or adjusted under 35 U.S.C. 154(b) by 342 days.

(21) Appl. No.: 18/317,784

(22) Filed: May 15, 2023

(65) Prior Publication Data

US 2023/0371793 A1    Nov. 23, 2023

Related U.S. Application Data

(60) Provisional application No. 63/364,928, filed on May 18, 2022.

(51) Int. Cl.
  *A61B 1/00*      (2006.01)
  *A61B 1/005*     (2006.01)
  *A61B 1/018*     (2006.01)

(52) U.S. Cl.
  CPC ...... *A61B 1/00128* (2013.01); *A61B 1/00094* (2013.01); *A61B 1/00101* (2013.01); *A61B 1/00142* (2013.01); *A61B 1/00165* (2013.01); *A61B 1/0052* (2013.01); *A61B 1/018* (2013.01)

(58) Field of Classification Search
  CPC ............ A61B 1/00094; A61B 1/00101; A61B 1/00142; A61B 1/00165; A61B 1/0052; A61B 1/018; A61B 1/00105; A61B 1/00071; A61B 1/0055; A61B 1/0011; A61B 1/005; A61B 1/00112–00128; A61B 1/00119; A61B 1/0057
  USPC ........................................................ 600/136
  See application file for complete search history.

(56) References Cited

U.S. PATENT DOCUMENTS

| | | | | |
|---|---|---|---|---|
| 4,534,339 A | * | 8/1985 | Collins | A61B 1/00128 600/146 |
| 4,911,148 A | * | 3/1990 | Sosnowski | A61B 1/00165 600/164 |
| 5,630,787 A | * | 5/1997 | Yabe | A61B 1/012 600/122 |
| 8,622,893 B2 | * | 1/2014 | Mathieu | A61M 39/1011 600/146 |

(Continued)

FOREIGN PATENT DOCUMENTS

JP          2002233491     *   8/2002

*Primary Examiner* — Anh Tuan T Nguyen
*Assistant Examiner* — Li-Ting Song
(74) *Attorney, Agent, or Firm* — Schwegman Lundberg & Woessner, P.A.

(57) ABSTRACT

An assembly can include a first component having at least one drainage channel and at least one fluid channel. The assembly can also include a second component having at least one drainage channel and at least one fluid channel. The assembly can also include a quick-connect coupling. The quick-connect coupling can be configured to couple the first component and the second component, fluidically connect the at least one drainage channel of the first component to the at least one drainage channel of the second component, and fluidically connect the at least one fluid channel of the first component to the at least one fluid channel of the second component.

13 Claims, 9 Drawing Sheets

(56)             References Cited

U.S. PATENT DOCUMENTS

| | | | |
|---|---|---|---|
| 2006/0287576 A1* | 12/2006 | Tsuji | A61B 1/00105 |
| | | | 600/132 |
| 2007/0162095 A1* | 7/2007 | Kimmel | A61B 1/042 |
| | | | 600/172 |
| 2008/0119695 A1* | 5/2008 | Ueno | A61B 1/0016 |
| | | | 600/152 |
| 2008/0214896 A1* | 9/2008 | Krupa | A61B 1/0653 |
| | | | 600/141 |
| 2009/0299344 A1* | 12/2009 | Lee | A61B 1/00042 |
| | | | 606/1 |
| 2010/0217082 A1* | 8/2010 | Ito | G02B 23/2476 |
| | | | 600/121 |
| 2012/0004503 A1* | 1/2012 | Kawaura | A61B 1/00128 |
| | | | 600/104 |
| 2012/0116167 A1* | 5/2012 | Shibuya | A61B 1/00091 |
| | | | 600/153 |
| 2017/0071447 A1* | 3/2017 | Nishiie | A61B 1/00112 |
| 2019/0313881 A1* | 10/2019 | Francher | A61B 1/00052 |
| 2019/0328212 A1* | 10/2019 | Nakaji | A61B 1/00071 |
| 2020/0060519 A1* | 2/2020 | Wake | A61B 1/126 |
| 2021/0068625 A1* | 3/2021 | Shin | A61B 1/0057 |
| 2021/0212553 A1* | 7/2021 | Appling | A61B 1/00042 |
| 2021/0315446 A1* | 10/2021 | Crawford | A61B 1/00177 |
| 2022/0265967 A1* | 8/2022 | Alhadeff | A61B 1/00105 |
| 2022/0323166 A1* | 10/2022 | Tilson | A61B 1/01 |
| 2023/0011670 A1* | 1/2023 | Kohanfars | A61B 1/00119 |
| 2023/0023094 A1* | 1/2023 | Dixson | A61B 1/015 |
| 2023/0165436 A1* | 6/2023 | Lund | A61B 1/00066 |
| | | | 600/131 |
| 2023/0172433 A1* | 6/2023 | Levinson | A61B 1/00066 |
| | | | 600/109 |
| 2024/0268652 A1* | 8/2024 | Arp | A61B 1/018 |
| 2024/0341572 A1* | 10/2024 | Patel | A61B 1/00027 |

* cited by examiner

QUICK CONNECT SUB-ASSEMBLIES FOR SCOPES

CROSS-REFERENCE TO RELATED APPLICATIONS

This application based upon and claims the benefit of priority from U.S. Provisional Patent Application Ser. No. 63/364,928, filed on May 18, 2022, the entire contents of which are incorporated herein by reference.

TECHNICAL FIELD

This disclosure relates generally to medical tools, and more particularly, to sub-assemblies of medical tools.

BACKGROUND

Conventional endoscopes can be used in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, providing suction passageways for collecting fluids (e.g., saline or other preparations), and the like. Such anatomical regions can include the gastrointestinal tract (e.g., esophagus, stomach, duodenum, pancreaticobiliary duct, intestines, colon, and the like), renal area (e.g., kidney(s), ureter, bladder, urethra), other internal organs (e.g., reproductive systems, sinus cavities, submucosal regions, respiratory tract), and the like.

SUMMARY

The inventors of the present disclosure have discovered at least the following trends in endoscopic technologies: 1) a desire and mandates to reduce medical waste, 2) hospitals and providers requiring equipment to be recycled, and 3) hospitals and providers requesting products that can be remanufactured. To keep up with these trends, the inventors of the present disclosure have identified at least the following problems with endoscopic technologies: 1) difficulty in the disassembly, 2) difficulty in the re-constructability, and 3) the accuracy of reconstruction of the endoscope. At least the following examples can be potential solutions to the above-identified problems.

In examples, an endoscope can include a control head including a body extending between a first end and a second end. The control head can include at least one control knob configured to manipulate an articulation wire. The endoscope can also include an insertion tube removably coupled to the control head. The insertion tube can extend between a first end and a distal tip. The insertion tube can include an articulation wire complementary to the articulation wire of the control head. The endoscope can also include a quick-connect coupling configured to couple the second end of the control head and the first end of the insertion tube to enable the articulation wire of the control head and the articulation wire of the insertion tube to mechanically communicate therethrough such that moving the at least one control knob of the control head manipulates the articulation wire of the control head and the articulation wire of the insertion tube.

In examples, an assembly can include a first component having at least one drainage channel and at least one fluid channel. The assembly can also include a second component having at least one drainage channel and at least one fluid channel. The assembly can also include a quick-connect coupling. The quick-connect coupling can be configured to couple the first component and the second component, fluidically connect the at least one drainage channel of the first component to the at least one drainage channel of the second component, and fluidically connect the at least one fluid channel of the first component to the at least one fluid channel of the second component.

In examples, a method for reprocessing an instrument for surgery may be provided. The instrument can have a control head with a body extending between a first end and a second end. The control head can include an articulation wire extending from a control knob and through the body to the second end of the control head. The instrument can also have an insertion tube removably coupled to the control head. The insertion tube can include an articulation wire complementary to the articulation wire of the control head and a quick-connect coupling configured to couple the second end of the control head to the first end of the insertion tube. The quick-connect coupling can also be configured to enable the articulation wire of the control head and the articulation wire of the insertion tube to mechanically communicate therethrough such that moving the control knob of the control head manipulates the articulation wire of the control head and the articulation wire of the insertion tube. The method can include obtaining the instrument, preparing the articulation wire for decoupling by setting the control knob on the control head to a zero position, and disconnecting the control head from the insertion tube by decoupling the quick-connect coupling. The method also includes removing the control knobs and preparing the control knobs for recycling, sanitizing the control head, and storing the control head in a sterile container.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

This disclosure relates to quick-connect sub-assemblies for endoscopes. Endoscopes can be used in various surgeries and procedures. Endoscopes can include expensive components that would be best recycled or reused. However, the sanitation and preparation of the endoscope for reuse is presently difficult because endoscopes do not include quick-connect sub-assemblies that can be taken apart for cleaning and sanitation. An endoscope with quick-connect sub-assemblies can include a light source module attached via a first quick-connect coupling to an umbilical cord. The umbilical cord can be attached to a control head via a second quick-connect coupling. The first quick-connect coupling and the second quick-connect coupling can be the same. The control head can be attached to an insertion tube via a third quick-connect coupling. Each of the first, second, and third quick-connect couplings can be configured to permit fluidical, optical, and electronic communication therethrough. Moreover, the control head can include a removable clamshell that can protect the control head from debris during procedures and be removed for cleaning and sanitation between procedures. Each of the components of the endoscope can be decoupled to prepare for recycling, cleaning, and sanitation, and/or reuse.

The above discussion is intended to provide an overview of subject matter of the present patent application. It is not intended to provide an exclusive or exhaustive explanation of the invention. The description below is included to provide further information about the present patent application. The endoscope with quick-connect sub-assemblies will be discussed with reference to FIGS. 1-8 below.

Figure 1:
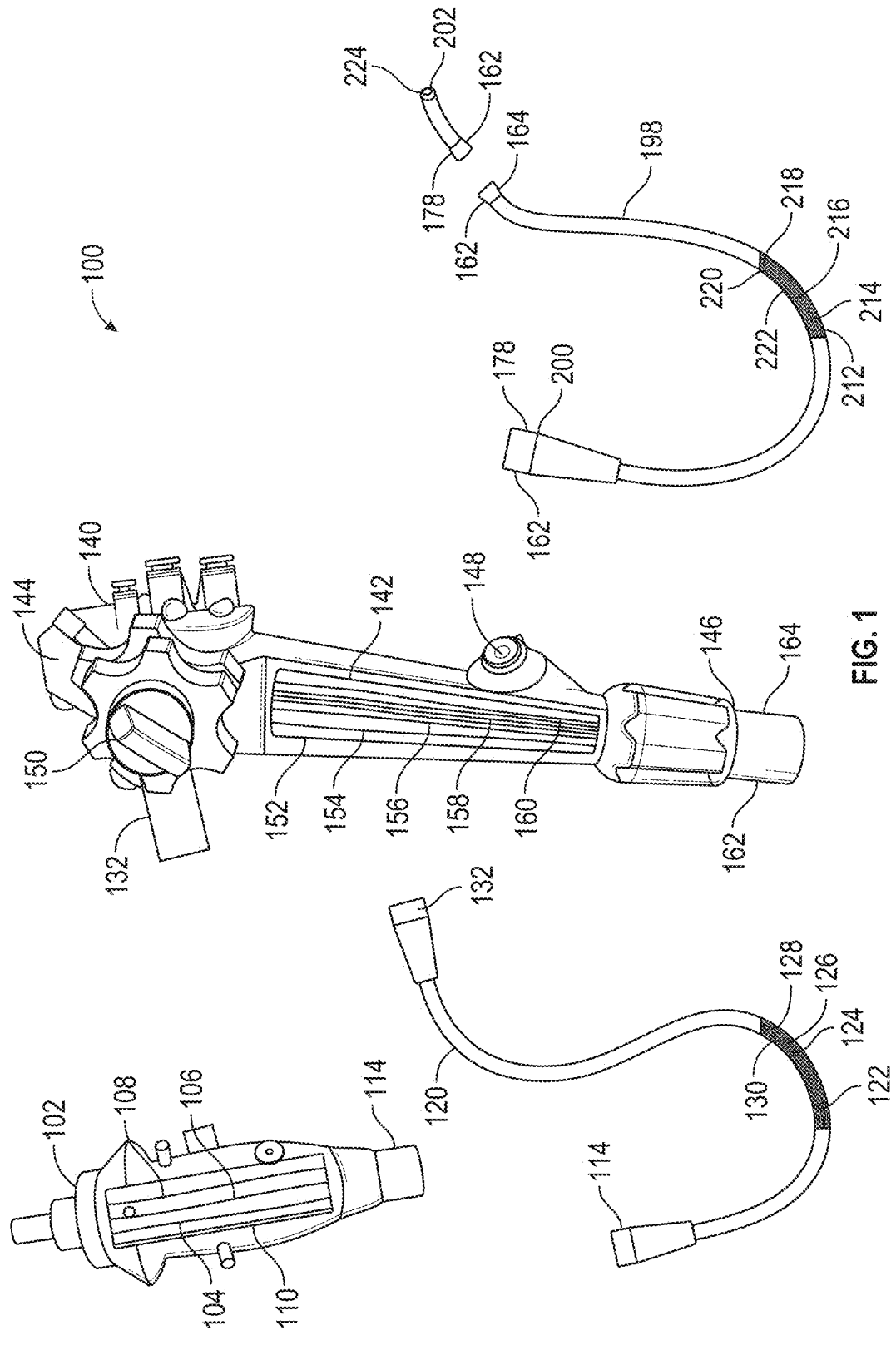
FIG. 1 illustrates a disassembled endoscope, in accordance with at least one example of the present disclosure.

FIG. 1 illustrates a portion of a disassembled endoscope, in accordance with at least one example of the present disclosure. An endoscope 100 can be configured to be inserted into a patient for one or more procedures. The endoscope 100 can be insertable into an anatomical region for imaging or to provide passage of or attachment to (e.g., via tethering) one or more sampling devices for biopsies, or one or more therapeutic devices for treatment of a disease state associated with the anatomical region. For example, the endoscope 100 can be a gastroscope, duodenoscope, ultrasound endoscope, ureteronrenoscope, hysteroscope, percutaneous nephroscope, colonoscope, bronchoscope, laparoscope, cystoscope, choledoschoscope, ear nose and throat ("ENT") endoscope, or any other kind of endoscope that can be inserted into a patient. As shown in FIG. 1, the endoscope 100 can include a light source module 102, a first auxiliary quick-connect coupling 114, an umbilical cord 120, a second auxiliary quick-connect coupling 132, a control head 140, a primary quick-connect coupling 162, and an insertion tube 198.

The light source module 102 can be configured to transmit light, electricity, and a suction lumen for the endoscope 100 from one or more control systems (not shown). In examples, the one or more control systems can be a surgical imaging system, a video system, or any other control system that can be connected to the endoscope 100. The light source module 102 can include one or more light guide fibers 104, one or more suction lines 106, one or more electrical lines 108, and one or more fluid lines 110.

The light guide fiber 104 can be configured to transmit a light from the control system through the light source module 102. For example, the one or more light guide fibers 104 can extend through the light source module 102. The one or more light guide fibers 104 can include one or more fibers that can optically transfer light.

The one or more suction lines 106 can be configured to permit debris, fluid, or any other matter to be sucked through the light source module 102. In examples, a control system can provide a suction force, for example, the control system can include a vacuum that is configured to remove fluid, debris, or any other matter from the one or more suction lines 106 of the light source module 102.

The one or more electrical lines 108 can be configured to permit electrical communication through the light source module 102. For example, the one or more electrical lines 108 can be a wire, cable, or any other line that can transmit electrical communication. In examples, the one or more electrical lines 108 can electronically connect the light source module 102 and the first auxiliary quick-connect coupling 114.

The one or more fluid lines 110 can be configured to permit fluidic communication through the light source module 102. For example, the one or more fluid lines 110 can be used to transport air, water, saline, or any other fluid through the light source module 102.

The first auxiliary quick-connect coupling 114 can be configured to couple the light source module 102 to the umbilical cord 120 and permit optical, fluidic, and electrical communication between the light source module 102 and the umbilical cord 120. The first auxiliary quick-connect coupling 114 will be discussed in more detail below with reference to FIG. 6.

The umbilical cord 120 can be configured to fluidically, electrically, and optically connect the first auxiliary quick-connect coupling 114 and the second auxiliary quick-connect coupling 132. The umbilical cord 120 can include a suction line 122, one or more fluid channels 126, at least one electrical line 128, and one or more light guide fibers 130. The suction line 122 can be configured to permit debris, fluid, or any other matter to be suctioned through the umbilical cord 120. In examples, the suction line 122 can also act as a working channel for the endoscope 100 such that tools, scalpels, or any other instruments can be inserted through the suction line 122 of the umbilical cord 120. The suction line 122 can extend an entire length of the umbilical cord 120. The fluid channel 126 can be configured to permit fluid flow through the umbilical cord 120. In examples, the fluid channel 126 can permit air, water, saline, or any other fluid through the umbilical cord 120. The fluid channel 126 can extend an entire length of the umbilical cord 120. The at least one electrical line 128 can be configured to permit electrical flow through the umbilical cord 120. The at least one electrical line 128 can extend an entire length of the umbilical cord 120. The one or more light guide fibers 130 can be configured to permit optical flow through the umbilical cord 120. The one or more light guide fibers 130 can extend the entire length of the umbilical cord 120.

The second auxiliary quick-connect coupling 132 can be configured to couple the umbilical cord 120 to the control head 140 and permit optical, fluidic, and electrical communication between the umbilical cord 120 and the control head 140. The second auxiliary quick-connect coupling 132 can be the same as the first auxiliary quick-connect coupling 114. Thus, the second auxiliary quick-connect coupling 132 will be discussed in more detail below with reference to FIG. 6.

The control head 140 can be configured to control the endoscope 100 as the insertion tube 198 is inserted into a patient. The control head 140 can include a body 142, at least one control knob 150, at least one articulation wire 152, a light guide fiber 154, at least one fluid channel 156, a suction channel 158, and one or more electrical lines 160.

The body 142 can be configured to fit within the hand of an operator. For example, the body 142 can be an elongated body that can extend between a first end 144 and a second end 146. The body 142 can provide protection to the other components of the control head 140. The body 142 can include an aperture formed in the side. For example, the body 142 can include an aperture 148. The aperture 148 can allow one or more tools to be inserted into a working channel, suction channel, or a lumen within the body 142.

The at least one control knob 150 can be configured to control the at least one articulation wire to manipulate the insertion tube 198 within the patient. For example, rotating the at least one control knob 150 in a first direction can move an articulation wire in a first direction and rotating the at least one control knob 150 in a second direction can move the articulation wire in a second direction. The first direction and the second direction can be opposite one another.

In one or more examples, the control head 140 can include multiple of the at least one control knob 150. For example, one of the at least one control knob 150 can control motion on a first plane. A second of the at least one control knob 150 can control motion of the insertion tube 198 on a second plane essentially perpendicular to the first plane. A third of the at least one control knob 150 can control motion of the insertion tube 198 on a third plane orthogonal to the first plane and the second plane. In another example, the control head 140 can include any number of the at least one control knob 150 to increase the control of the insertion tube 198 within a patient.

The at least one articulation wire 152 can be configured to move in reaction to manipulation of the at least one control knob 150. The at least one articulation wire 152 can extend from the first end 144 to the second end 146 of the body 142. In examples, the at least one articulation wire 152 can be mechanically attached to the at least one control knob 150.

The light guide fiber 154 can be configured to transmit light through the control head 140. The light guide fiber 154 can extend from the body 142 to the first end 144 of the body 142. In examples, the light guide fiber 154 can include one or more fibers that can optically transfer light.

The at least one fluid channel 156 can be configured to permit fluid flow through the control head 140. The at least one fluid channel 156 can extend from one or more fittings (not shown) that extend through the body 142 of the control head 140 to the first end 144 of the body 142. In examples, water, saline, or any other fluid can be introduced to the at least one fluid channel 156 of the control head 140 through the fittings extending through the body 142 of the control head 140.

The suction channel 158 can be configured to permit debris, fluid, or any other matter to be sucked through the control head 140. In examples, the suction channel 158 can be a lumen that can also work as a working channel for the endoscope 100. In such examples, tools, scalpels, or any other instrument that can be used during an endoscopic procedure. Thus, the suction channel 158 can be able to simultaneously suction debris, fluid, or other matter through the suction channel 158 while providing one or more tools or instruments to the endoscope 100.

The one or more electrical lines 160 can be configured to permit electrical communication through the control head 140. For example, the one or more electrical line 160 can be a wire, cable, or any other line that can transmit electrical communication. In examples, the one or more electrical line 160 can electronically connect the second auxiliary quick-connect coupling 132 and the primary quick-connect coupling 162.

The primary quick-connect coupling 162 can be configured to couple the control head 140 and the insertion tube 198 and permit optical, fluidic, electrical, and mechanical communication between the control head 140 and the insertion tube 198. The primary quick-connect coupling 162 will be discussed with more detail with reference to FIGS. 3A and 3B below.

In another example, as shown in FIG. 1, the primary quick-connect coupling 162 can be configured to couple the insertion tube 198 to a removable tip 224. When coupled to the insertion tube 198 the removable tip 224 forms a distal tip 202. The removable tip 224 can include a light, camera, one or more fluid outlets, one or more working channels or lumens, or any other components used at the distal tip of an insertion tube on an endoscope.

Figure 2B:
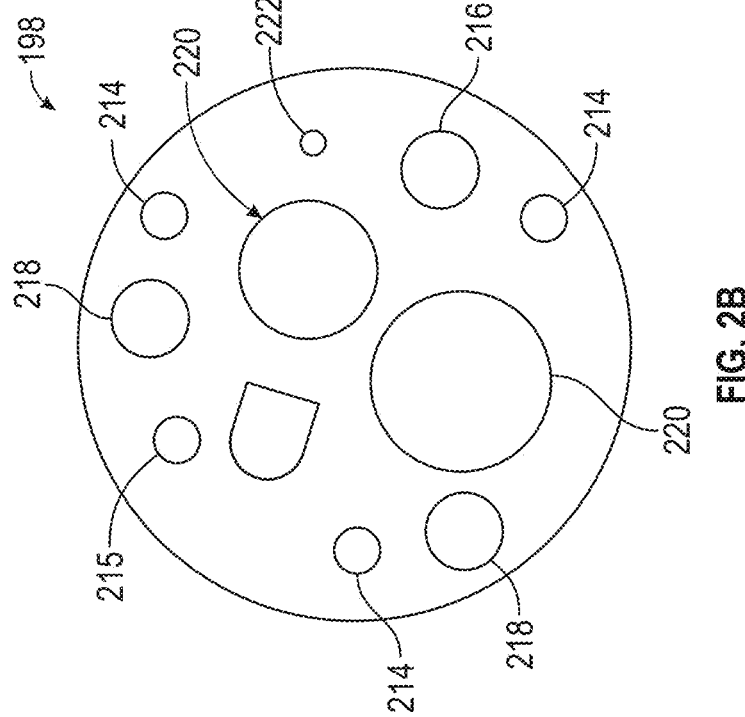
FIG. 2B illustrates a cross-sectional view of a portion of a shell of the insertion tube of FIG. 2A taken along line 2B-2B, in accordance with at least one example of the present disclosure.
Figure 2A:
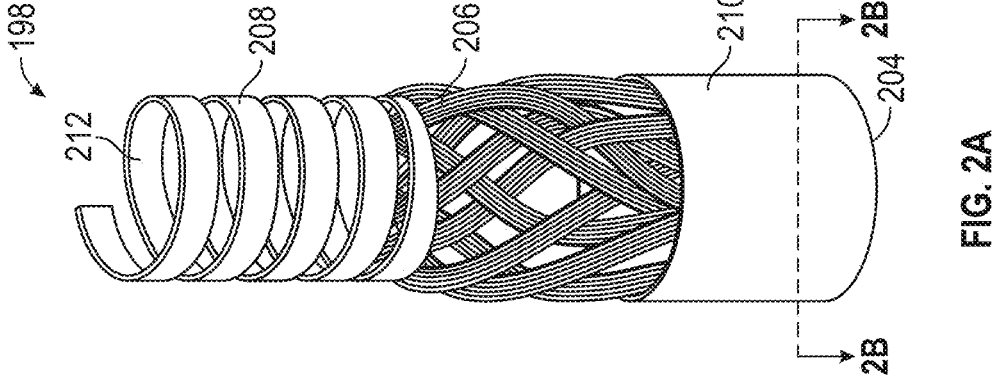
FIG. 2A illustrates a perspective view of a portion of a shell of an insertion tube, in accordance with at least one example of the present disclosure.

The insertion tube 198 can be configured to be inserted into a patient. The insertion tube 198 can extend between a first end 200 and the distal tip 202. The insertion tube 198 will be discussed in more detail with reference to FIGS. 2A and 2B below. FIG. 2A illustrates a perspective view of a portion of a shell 204 of the insertion tube 198. FIG. 2B illustrates a cross-sectional view of the portion of the shell of the insertion tube of FIG. 2A taken along line 2B-2B.

The shell 204 of the insertion tube 198 can be configured to protect all the components within the insertion tube 198 and can be flexible such that the shell 204 can navigate within a patient during an endoscopic procedure. In examples, the shell 204 can be layered. For example, the shell 204 can include a stainless-steel mesh 206, a spiral-metal band 208, and a polymer coat 210. The shell 204 can be hollow such that all the channels, lines, wires, and lumens can extend through the insertion tube 198. For example, the shell 204 can define a lumen 212 that can extend from the first end 200 to the distal tip 202 of the insertion tube 198.

The stainless-steel mesh 206 can be configured to define an inner diameter of the shell 204 of the insertion tube 198. More particularly, the stainless-steel mesh 206 can define the lumen 212 of the insertion tube 198. The stainless-steel mesh 206 can extend from the first end 200 to the distal tip 202. The stainless-steel mesh 206 can be configured to support and hold each of the components within the insertion tube 198. The stainless-steel mesh 206 can enable the shell 204 to be flexible. The flexibility that the stainless-steel mesh 206 provides to the shell 204 can help navigate the insertion tube 198 within a patient during an endoscopic procedure.

The spiral-metal band 208 can be configured to support the insertion tube 198. The spiral-metal band 208 can extend from the first end 200 to the distal tip 202 of the insertion tube 198. The spiral-metal band 208 can help protect the components within the insertion tube 198. In examples, the spiral-metal band 208 can increase the stiffness of the insertion tube 198 to help the insertion tube 198 navigate through a patient during an endoscopic procedure.

The polymer coat 210 can be configured to fluidically seal the insertion tube 198. The polymer coat 210 can extend from the first end 200 to the distal tip 202 of the insertion tube 198. The polymer coat 210 can fluidically seal the insertion tube 198 such that any liquids within the insertion tube 198 remain within the first end 200 and any liquids within a patient not flowing through the suction channel 158 remain outside of the first end 200 of the insertion tube 198. The polymer coat 210 can be made from any impermeable polymer that can be inserted into a human body.

As shown in the example illustrated in FIG. 2B, the insertion tube 198 can include at least one articulation wire 214, a stiffness wire 215, at least one light guide fiber 216, at least one fluid channel 218, and at least one suction channel 220.

The at least one articulation wire 214 can be configured to manipulate the insertion tube 198 within a patient during an endoscopic procedure. The at least one articulation wire 214 can extend within the lumen 212 from the first end 200 to the distal tip 202. The at least one articulation wire 214 can be configured to be complementary to the at least one articulation wire 152 of the control head 140. The interactions between the at least one articulation wire 152 and the at least one articulation wire 214 will be discussed below with reference to FIGS. 3A-5C.

The stiffness wire 215 can be configured to add stiffness to the insertion tube 198 to aid in the navigation of the insertion tube 198 within the body of a patient during an endoscopic procedure. The stiffness wire 215 can extend within the lumen 212 from the first end 200 to the distal tip 202.

The at least one light guide fiber 216 can be configured to transmit light through the insertion tube 198. The at least one light guide fiber 216 can extend from the first end 200 through the distal tip 202 of the insertion tube 198. The at least one light guide fiber 216 can be one or more fibers that can transmit optical signals. The at least one light guide fiber 216 can be configured to be complementary to the light guide fiber 154 of the control head 140 and the one or more light guide fibers 104 of the light source module 102. The interactions between the one or more light guide fibers 104, the light guide fiber 154, and the at least one light guide fiber 216 will be discussed below with reference to FIGS. 3A, 3B, 6, and 7.

The at least one fluid channel 218 can be configured to permit fluid flow through the insertion tube 198. The at least one fluid channel 218 can extend within the lumen 212 from the first end 200 through the distal tip 202 of the insertion tube 198. The at least one fluid channel 218 can be configured to be complementary to the at least one fluid channel 156 of the control head 140 and the one or more fluid lines 110 of the light source module 102. The interactions between the one or more fluid lines 110, the at least one fluid channel 156, and the at least one fluid channel 218 will be discussed below with reference to FIGS. 3A-3B.

The at least one suction channel 220 can be configured to permit debris, fluid, or any other matter to be sucked through the insertion tube 198. In examples, the suction channel 220 can be a lumen that can also work as a working channel for the endoscope 100. In such examples, tools, scalpels, or any other instrument that can be used during an endoscopic procedure. Thus, the suction channel 220 can be able to simultaneously suction debris, fluid, or other matter through the suction channel 220 while providing one or more tools or instruments to the endoscope 100. The at least one suction channel 220 can be configured to be complementary with the suction channel 158 of the control head 140 and the one or more suction lines 106 of the light source module 102. The interactions between the one or more suction lines 106, the suction channel 158, and the at least one suction channel 220 will be discussed below with reference to FIGS. 3A, 3B, 6, and 7 below.

The one or more electrical lines 222 can be configured to supply electrical power to any device or system within the insertion tube 198. For example, the one or more electrical lines 222 can provide power to a camera, an auxiliary tool, or any other device used in an endoscopic procedure.

Figure 3B:
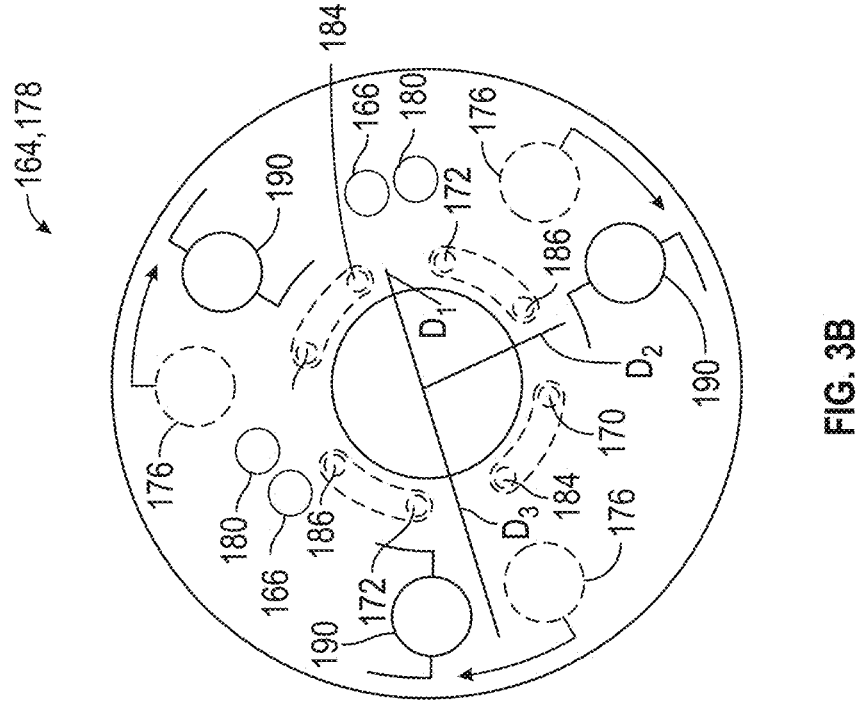
FIG. 3B is a cross-sectional view of the quick-connect coupling of FIG. 3A taken along line 3B-3B, in accordance with at least one example of the present disclosure.
Figure 3A:
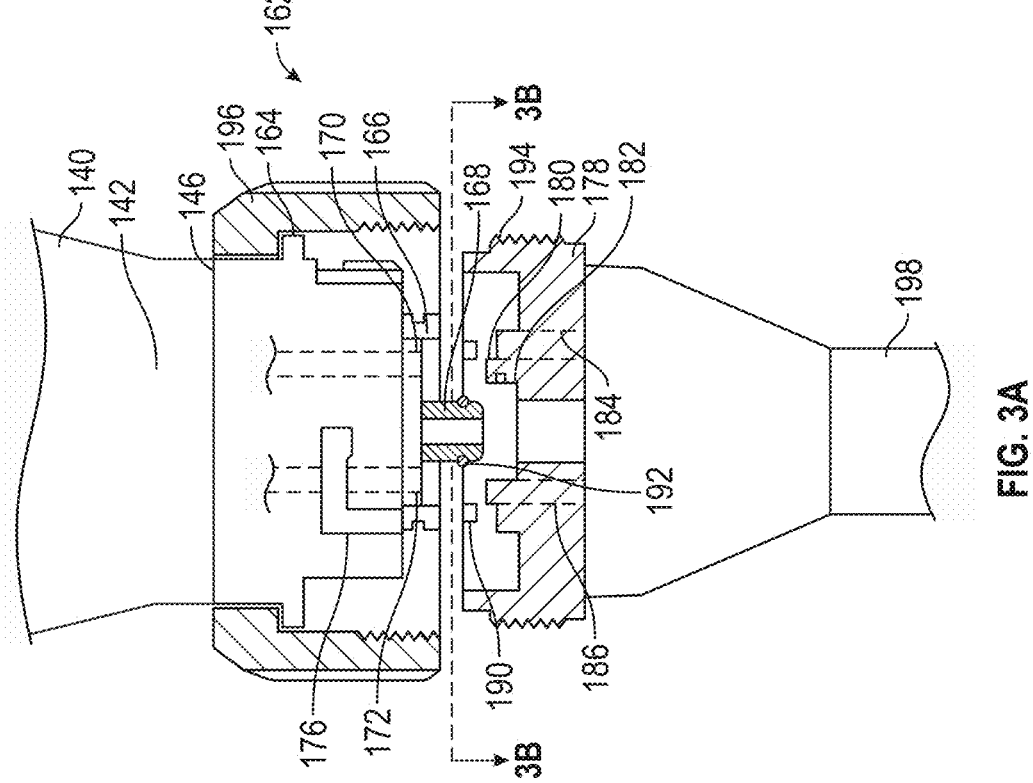
FIG. 3A is a perspective view of a quick-connect coupling, in accordance with at least one example of the present disclosure.

FIG. 3A is a perspective view of a quick-connect coupling, in accordance with at least one example of the present disclosure. For example, the quick-connect coupling shown in FIG. 3A can be primary quick-connect coupling 162. The primary quick-connect coupling 162 can be configured to removably couple the control head 140 and the insertion tube 198. The primary quick-connect coupling 162 can include a first portion 164, a second portion 178, and a threaded collar 196.

The first portion 164 of the primary quick-connect coupling 162 can be configured to enable connection of the control head 140 to the second portion 178 of the primary quick-connect coupling 162. In examples, the first portion 164 can be integral to the second end 146 of the body 142. For example, the first portion 164 can be formed in the second end 146 of the body 142. In another example, the first portion 164 can be removably attached to the second end 146 of the body 142. The first portion 164 can include at least one articulation wire coupling 166, a suction line fitting 168, at least one fluid line outlet 170, a light guide fiber outlet 172, and at least two twist-lock grooves 176.

The at least one articulation wire coupling 166 can be configured to couple the at least one articulation wire 152 of the control head 140 to the at least one articulation wire coupling 180 of the second portion 178 of the primary quick-connect coupling 162. In examples, the at least one articulation wire coupling 166 can be integral to the at least one articulation wire 152 of the control head 140. In another example, the at least one articulation wire coupling 166 can be removably attached to the at least one articulation wire 152 of the control head 140.

The suction line fitting 168 can be configured to fluidically connect the suction channel 158 of the control head 140 and the second portion 178 of the primary quick-connect coupling 162. More specifically, the suction line fitting 168 can fluidically connect the suction channel 158 of the control head 140 and the suction line receptacle 182 of the second portion 178 of the primary quick-connect coupling 162. In one example, the suction line fitting 168 can be integral the suction channel 158 of the control head 140. For example, the suction line fitting 168 can be formed in the suction channel 158 at the second end 146 of the body 142. In another example, the suction line fitting 168 can be removably coupled to the suction channel 158 of the control head 140. The suction line fitting 168 can include one or more O-rings 192. The one or more O-rings 192 can help fluidically seal the suction line fitting 168 and the suction line receptacle 182 of the second portion 178.

The at least one fluid line outlet 170 can be configured to fluidically connect the at least one fluid channel 156 of the control head 140 and the second portion 178 of the primary quick-connect coupling 162. More specifically, the at least one fluid line outlet 170 can fluidically connect the at least one fluid channel 156 of the control head 140 to the at least one fluid line receptacle 184 of the second portion 178 of the primary quick-connect coupling 162. The at least one fluid line outlet 170 can be integral the at least one fluid channel 156. In another example, the at least one fluid line outlet 170 can be removably attached to the at least one fluid channel 156.

The light guide fiber outlet 172 can be configured to optically connect the light guide fiber 154 of the control head 140 and the second portion 178 of the primary quick-connect coupling 162. More specifically, the light guide fiber outlet 172 can optically connect the light guide fiber 154 of the control head 140 to the light guide fiber inlet 186 of the second portion 178 of the primary quick-connect coupling 162. Moreover, the light guide fiber outlet 172 can align a centerline of the light guide fiber 154 and a centerline of the light guide fiber inlet 186 of the second portion 178. Aligning the centerline of the light guide fiber 154 and the light guide fiber inlet 186 can permit optical communication through the primary quick-connect coupling 162 without distorting, deflecting, or refracting a light signal through the primary quick-connect coupling 162.

The at least two twist-lock grooves 176 can be configured to receive the at least two twist-lock protrusions 190 to hold the first portion 164 and the second portion 178 together after the first portion 164 and the second portion 178 are engaged with one another.

The second portion 178 of the primary quick-connect coupling 162 can be configured to enable connection of the insertion tube 198 to the first portion 164 of the primary quick-connect coupling 162. In examples, the second portion 178 can be integral to the first end 200 of the insertion tube 198. For example, the second portion 178 can be formed in the first end 200 of the insertion tube 198. In another example, the second portion 178 can be removably attached to the first end 200 of the insertion tube 198. The second portion 178 can include at least one articulation wire coupling 180, a suction line receptacle 182, at least one fluid line receptacle 184, a light guide fiber inlet 186, at least two twist-lock protrusions 190, and a threaded surface 194 formed on an outer periphery of the second portion 178.

The at least one articulation wire coupling 180 can be configured to couple the at least one articulation wire 214 of the insertion tube 198 to the at least one articulation wire coupling 166 of the first portion 164 of the primary quick-connect coupling 162. In examples, the at least one articulation wire coupling 180 can be integral the at least one articulation wire 214 of the insertion tube 198. In another example, the at least one articulation wire coupling 180 can be removably attached to the at least one articulation wire 214 of the insertion tube 198.

When the at least one articulation wire coupling 166 and the at least one articulation wire coupling 180 are engaged with one another, the at least one articulation wire coupling 166 can transfer forces imposed on the at least one articulation wire 152 by the at least one control knob 150 to the at least one articulation wire coupling 180. The at least one articulation wire coupling 180 can be configured to transfer the force imposed on the at least one articulation wire 152 by the at least one control knob 150 to the at least one articulation wire 214 of the insertion tube 198. Thus, as an operator can articulate the at least one control knob 150 on the control head 140 to manipulate the insertion tube 198 of the endoscope 100. The engagement of the at least one articulation wire coupling 166 and the at least one articulation wire coupling 180 will be discussed below with reference to FIGS. 4A-5C below.

The suction line receptacle 182 can be configured to receive the suction line fitting 168 such as to fluidically connect the suction channel 158 of the control head 140 to the at least one suction channel 220 of the insertion tube 198. In one or more examples, the suction line receptacle 182 can be integral the at least one suction channel 220 of the insertion tube 198. In another example, the suction line receptacle 182 can be removably coupled to the at least one suction channel 220 of the insertion tube 198.

When the suction line fitting 168 is inserted into the suction line receptacle 182, the suction channel 158 of the control head 140 and the at least one suction channel 220 of the insertion tube 198 can be fluidically connected such that the suction channel 158 and the at least one suction channel 220 can be used as a working channel for the endoscope 100. In examples, the suction channel 158 and the at least one suction channel 220 can be used to introduce tools, scalpels, or any other instrument that can be used during an endoscopic procedure, to the distal tip 202 of the insertion tube 198 while simultaneously removing debris, fluid, or other matter from in front of the distal tip 202 of the insertion tube 198. The O-rings 192 on the suction line fitting 168 can be configured to help fluidically seal the connection between the suction line fitting 168 and the suction line receptacle 182.

The at least one fluid line receptacle 184 can be configured to receive the at least one fluid line outlet 170 such as to fluidically connect the at least one fluid channel 156 of the control head 140 to the at least one fluid channel 218 of the insertion tube 198. In examples, the at least one fluid line receptacle 184 can be integral the first end 200 of the insertion tube 198. In another example, the at least one fluid line receptacle 184 can be removably coupled to the first end 200 of the insertion tube 198.

When the at least one fluid line outlet 170 is inserted into the at least one fluid line receptacle 184, the at least one fluid channel 156 and the at least one fluid channel 218 can be fluidically connected such that the at least one fluid channel 156 and the at least one fluid channel 218 can provide fluid to the distal tip 202 of the insertion tube 198. In examples, the at least one fluid channel 156 and the at least one fluid channel 218 can provide water, saline, air, or any other fluid used during an endoscopic procedure to the distal tip 202 of the insertion tube 198.

The light guide fiber inlet 186 can be configured to optically connect the first portion 164 of the primary quick-connect coupling 162 and the at least one light guide fiber 216 of the insertion tube 198. More specifically, the light guide fiber inlet 186 can optically connect the light guide fiber outlet 172 of the first portion 164 of the primary quick-connect coupling 162 to the at least one light guide fiber 216 of the insertion tube 198. Moreover, the light guide fiber inlet 186 can align a centerline of the light guide fiber outlet 172 of the first portion 164 and a centerline of the at least one light guide fiber 216 of the insertion tube 198. Aligning the centerline of the light guide fiber outlet 172 and the at least one light guide fiber 216 can permit optical communication through the primary quick-connect coupling 162 without distorting, deflecting, or refracting a light signal through the primary quick-connect coupling 162.

Thus, when the light guide fiber outlet 172 and the light guide fiber inlet 186 are engaged, the centerline of the light guide fiber 154 of the control head 140 and the centerline of the at least one light guide fiber 216 of the insertion tube 198 can be aligned. Therefore, when the light guide fiber outlet 172 and the light guide fiber inlet 186 are engaged, the light guide fiber 154 of the control head 140 and the at least one light guide fiber 216 of the insertion tube 198 can be in optical communication without distorting, deflecting, or refracting a light signal through the primary quick-connect coupling 162.

The at least two twist-lock protrusions 190 can be configured to be inserted into the at least two twist-lock grooves 176 to hold the first portion 164 and the second portion 178 together after the first portion 164 and the second portion 178 are engaged with one another. Each of the twist-lock grooves 176 and the at least two twist-lock protrusions 190 can be a different size to ensure that the first portion 164 and the second portion 178 are properly connected. For example, a first groove of the at least two twist-lock grooves 176 can be a first size and a second groove of the at least two twist-lock grooves 176 can be a second size, and a first protrusion of the at least two twist-lock protrusions 190 can be a first size and a second protrusion of the at least two twist-lock protrusions 190 can be a second size, such that the at least two twist-lock grooves 176 of the first size and the at least two twist-lock protrusions 190 of the first size can be configured to fit together and the at least two twist-lock grooves 176 of the second size and the at least two twist-lock protrusions 190 of the second size can be configured to fit together, respectively. The different sizes of the first portion 164 and the at least two twist-lock protrusions 190 can help ensure the first portion 164 and the second portion 178 of the primary quick-connect coupling 162 are correctly engaged with one another.

The threaded surface 194 can be formed on the periphery of the second portion 178 of the primary quick-connect coupling 162. In another example, the threaded surface 194 can be permanently or removably attached to the periphery of the second portion 178 of the primary quick-connect coupling 162. The threaded surface 194 can be complementary to the threaded collar 196 such that the threaded collar 196 can hold the first portion 164 and the second portion 178 of the primary quick-connect coupling 162 together.

The threaded collar 196 can be configured to engage with the threaded surface 194 on the periphery of the second portion 178 of the primary quick-connect coupling 162. The threaded collar 196 can be an annular body with a threaded surface facing inward. In examples, the threaded collar 196 can float on the second end 146 of the control head 140 and the first portion 164 of the primary quick-connect coupling 162. In examples, the threaded collar 196 can be moved to float around the second end 146 of the control head 140 while the first portion 164 and the second portion 178 are being coupled to each other. In another example, the threaded collar 196 can be moved to float around the first portion 164 after the first portion 164 and the second portion 178 are engaged with one another to position the threaded collar 196 in a position to engage with the threaded surface 194 on the periphery of the second portion 178 of the primary quick-connect coupling 162.

In one example, the threaded collar 196 can include a ridge configured to engage with the first portion 164 of the primary quick-connect coupling 162. For example, the ridge on the threaded collar 196 can exert an axial force on the first portion 164 when the threaded collar 196 is engaged with the threaded surface 194 of the second portion 178. The axial force exerted on the first portion 164 of the primary quick-connect coupling 162 can increase a static friction between the first portion 164 and the second portion 178 to help maintain engagement of the first portion 164 and the second portion 178 of the primary quick-connect coupling 162.

FIG. 3B is a cross-sectional view of the primary quick-connect coupling 162 of FIG. 3A taken along line 3B-3B, in accordance with at least one example of the present disclosure. As shown in FIG. 3B, the first portion 164 of the primary quick-connect coupling 162 can be generally circular and include a center point, a first diameter $D_1$, a second diameter $D_2$, and a third diameter $D_3$. In examples, the suction line fitting 168 can be concentrically centered on the center point of the first portion 164 such that the first portion 164 of the primary quick-connect coupling 162 is configured to rotate about the suction line fitting 168. The at least one fluid line outlet 170 and the light guide fiber outlet 172 can be spaced around the center point at the first diameter $D_1$. The at least one articulation wire coupling 166 can be spaced around the center point at the second diameter $D_2$. The at least two twist-lock grooves 176 can be spaced around the center point at a third diameter $D_3$.

Like the first portion 164, the second portion 178 of the primary quick-connect coupling 162 can be generally circular and include a center point, a first diameter $D_1$, a second diameter $D_2$, and a third diameter $D_3$. In examples, the suction line receptacle 182 can be concentrically centered on the center point of the second portion 178 such that the second portion 178 of the primary quick-connect coupling 162 is configured to rotate about the second portion 178. The at least one fluid line receptacle 184 and the light guide fiber inlet 186 can be spaced around the center point at the first diameter $D_1$. The at least one articulation wire coupling 180 can be spaced around the center point at the second diameter $D_2$. The at least two twist-lock protrusions 190 can be spaced around the center point at a third diameter $D_3$.

The first portion 164 and the second portion 178 having similar shapes (e.g., generally circular) and similar spacings of components around the center points enables the components of the first portion 164 and the components second portion 178 to align with one another when the first portion 164 is engaged with the second portion 178.

The first portion 164 and the second portion 178 of the primary quick-connect coupling 162 can be engaged by inserting the suction line fitting 168 into the suction line receptacle 182 such that the at least two twist-lock protrusions 190 fit within the at least two twist-lock grooves 176. After the suction line fitting 168 is inserted into the suction line receptacle 182 and the at least two twist-lock protrusions 190 are inserted into the at least two twist-lock grooves 176 the first portion 164 and the second portion 178 can be rotated in opposite directions to couple the first portion 164 and the second portion 178. When the first portion 164 and the second portion 178 are fully engaged, the at least two twist-lock protrusions 190 in the at least two twist-lock grooves 176 can prevent further rotation of the first portion 164 and the second portion 178.

When the first portion 164 and the second portion 178 are engaged, the at least one articulation wire coupling 166 can be coupled to the at least one articulation wire coupling 180 such that any forces applied to the at least one articulation wire coupling 166 by the at least one articulation wire 152 are transferred to the at least one articulation wire 214 by the at least one articulation wire coupling 180. Some examples of the connections between the first portion 164 and the second portion 178 will be discussed below with reference to FIGS. 4A-5C.

When the first portion 164 and the second portion 178 are engaged, the at least one fluid line outlet 170 and the at least one fluid line receptacle 184 can be aligned such that the first portion 164 and the at least one fluid line outlet 170 together fluidically connect the at least one fluid channel 156 of the control head 140 and the at least one fluid channel 218 of the insertion tube 198.

When the first portion 164 and the second portion 178 are engaged, the light guide fiber outlet 172 and the light guide fiber inlet 186 can relate to their centerlines aligned such that the light guide fiber outlet 172 and the light guide fiber inlet 186 optically connect the light guide fiber 154 of the control head 140 and the at least one light guide fiber 216 of the insertion tube 198. Alignment of the centerlines of the light guide fiber outlet 172 and the light guide fiber inlet 186 and the light guide fiber 154 and the at least one light guide fiber 216, respectively, can help reduce noise in a light signal caused by distortion, reflection, or refraction.

After the first portion 164 and the second portion 178 are engaged, the threaded collar 196 can be slid around the first portion 164 of the primary quick-connect coupling 162 such that the threaded collar 196 can engage the threaded surface 194 of the second portion 178 of the primary quick-connect coupling 162. The threaded collar 196 can be rotated around a center axis to engage the first portion 164 and maintain connection of the first portion 164 and the second portion 178 of the primary quick-connect coupling 162. In another example, the first portion 164 can include a clip that removably attaches to a ridge on the second portion 178 of the primary quick-connect coupling 162 to help maintain the connection between the first portion 164 and the second portion 178 when the first portion 164 and the second portion 178 are fully engaged. In another example, any other form of connector can be used to maintain the connection between the first portion 164 and the second portion 178 when the first portion 164 and the second portion 178 are fully engaged.

Figure 4B:
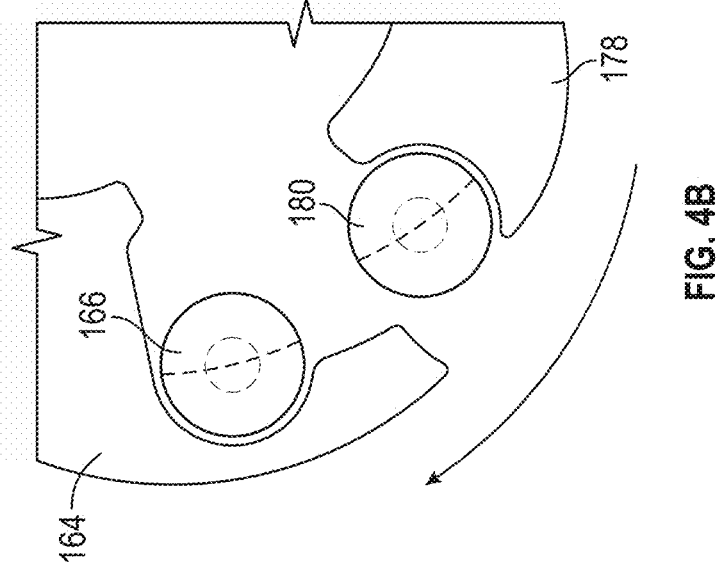
FIG. 4B is a top view of a portion of the quick-connect coupling during engagement, in accordance with at least one example of the present disclosure.
Figure 4A:
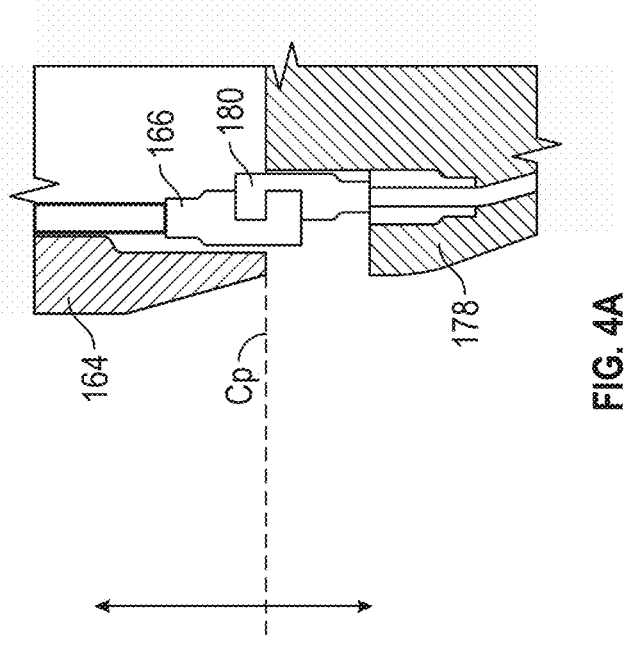
FIG. 4A is a perspective view of a portion of a quick-connect coupling, in accordance with at least one example of the present disclosure.

FIGS. 4A and 4B will be discussed together below. FIG. 4A is a partial cross-sectional view of an example of the primary quick-connect coupling 162. FIG. 4B is a top view of a portion of primary quick-connect coupling 162 during engagement.

As shown in FIG. 4A, the at least one articulation wire coupling 166 of the first portion 164 and the at least one articulation wire coupling 180 of the second portion 178 can be configured to couple to one another. In examples, the at least one articulation wire coupling 166 and the at least one articulation wire coupling 180 can each include a groove complementary to one another. For example, the at least one articulation wire coupling 166 and the at least one articulation wire coupling 180 can include groves such that the at least one articulation wire coupling 166 and the at least one articulation wire coupling 180 can slide together as the first portion 164 and the second portion 178 are engaged with one another. In examples, the at least one articulation wire coupling 166 and the at least one articulation wire coupling 180 can be the same component orientated in opposite positions.

As also shown in FIG. 4A, the at least one articulation wire coupling 166 and the at least one articulation wire coupling 180 can include a common plane CP. The common plane CP of the at least one articulation wire coupling 166 and the at least one articulation wire coupling 180 can be the plane at which the grooves in the at least one articulation wire coupling 166 and the at least one articulation wire coupling 180 can align so the at least one articulation wire coupling 166 and the at least one articulation wire coupling 180 can be coupled to one another. In examples, the at least one control knob 150 (FIG. 1) of the control head 140 (FIG. 1) can be used to position the at least one articulation wire coupling 166 along the common plane CP. For example, the 150/can be set to a zero position to There can be another tool, or any other way to adjust the at least one articulation wire coupling 180 to align the at least one articulation wire coupling 180 on the common plane.

The first portion 164 of the primary quick-connect coupling 162 can extend along the primary quick-connect coupling 162 up to the common plane CP of the at least one articulation wire coupling 166. Moreover, the second portion 178 of the primary quick-connect coupling 162 can extend along the at least one articulation wire coupling 180 up to the common plane CP of the at least one articulation wire coupling 180. The extension of the first portion 164 and the second portion 178 can provide support to the at least one articulation wire coupling 166 and the at least one articulation wire coupling 180, respectively. For example, the extension of the first portion 164 can prevent the at least one articulation wire coupling 166 from flexing or moving radially outward from the primary quick-connect coupling 162 when the at least one articulation wire coupling 166 and the at least one articulation wire coupling 180 are being coupled together. The extension of the second portion 178 can prevent the at least one articulation wire coupling 180 from flexing or moving radially inward the primary quick-connect coupling 162 when the at least one articulation wire coupling 166 and the at least one articulation wire coupling 180 are coupled together.

As shown in FIG. 4B, the first portion 164 of the primary quick-connect coupling 162 can be configured to at least partially surround the at least one articulation wire coupling 166 to provide lateral support to the at least one articulation wire coupling 166 while the at least one articulation wire coupling 166 is being engaged to the at least one articulation wire coupling 180. Moreover, the first portion 164 of the primary quick-connect coupling 162 can extend circumferentially around the periphery of the primary quick-connect coupling 162 such that the first portion 164 surrounds both the at least one articulation wire coupling 166 and the at least one articulation wire coupling 180 when the at least one articulation wire coupling 166 and the at least one articulation wire coupling 180 are coupled together. The circumferential extension of the first portion 164 can help align the first portion 164 and the at least one articulation wire coupling 180 as the primary quick-connect coupling 162 and the second portion 178 are coupled together.

The second portion 178 of the primary quick-connect coupling 162 can be configured to at least partially surround the at least one articulation wire coupling 180 to provide lateral support to the at least one articulation wire coupling 180 while the at least one articulation wire coupling 180 is being engaged to the at least one articulation wire coupling 166. The portion of the second portion 178 that at least partially surrounds the at least one articulation wire coupling 180 and the circumferential extension of the first portion 164 can together help guide the at least one articulation wire coupling 180 toward the at least one articulation wire coupling 166.

Figures 5A, 5B, 5C:
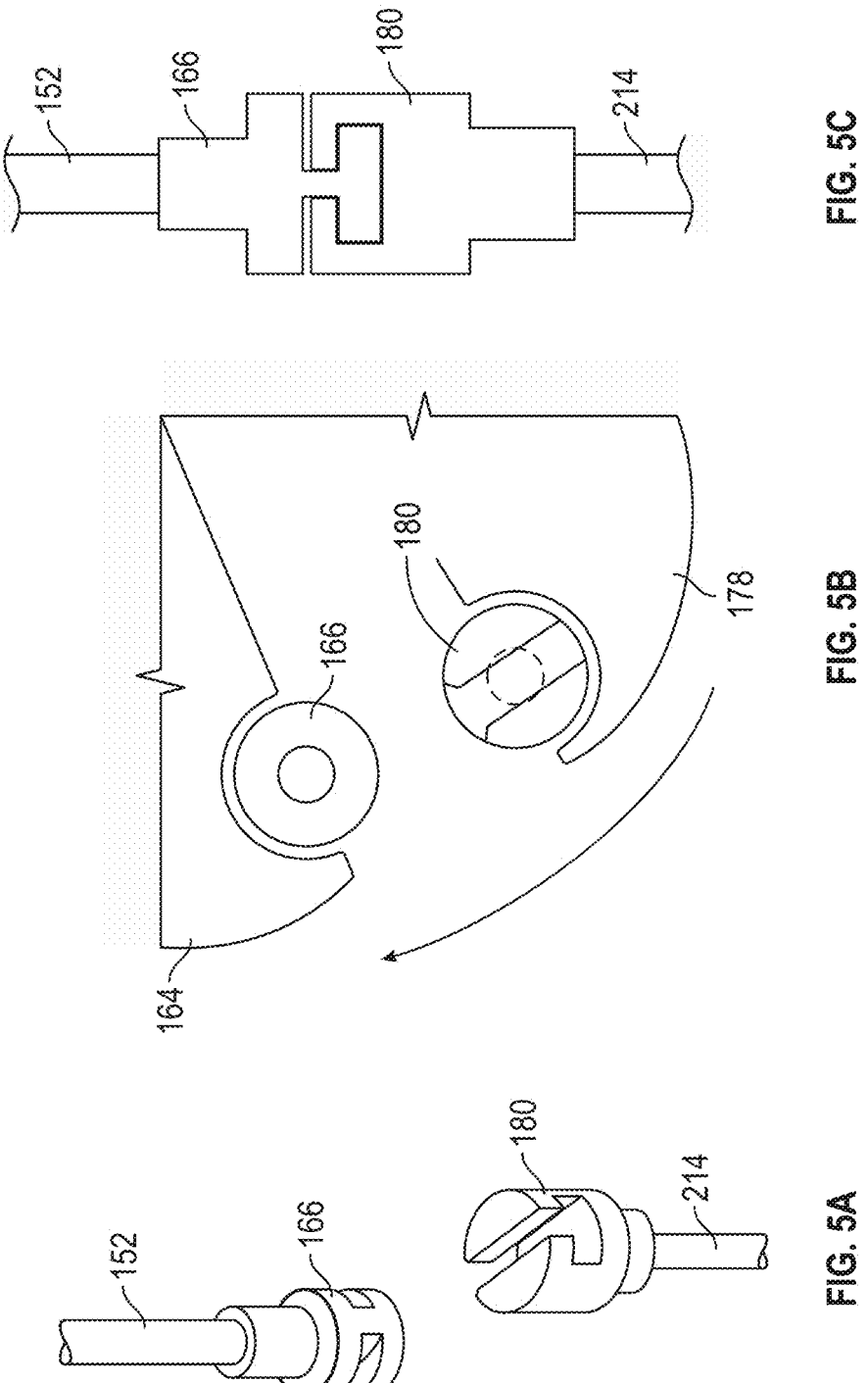
FIG. 5A is a perspective view of a portion of a quick-connect coupling before engagement, in accordance with at least one example of the present disclosure.
FIG. 5B is a top view of a portion of a quick-connect coupling during engagement, in accordance with at least one example of the present disclosure.
FIG. 5C is a perspective view of a portion of a quick-connect coupling after engagement, in accordance with at least one example of the present disclosure.

FIGS. 5A-5C can be discussed concurrently below. FIG. 5A is a perspective view of an example of a portion of primary quick-connect coupling 162 before engagement of the at least one articulation wire coupling 166 of the first portion 164 and the at least one articulation wire coupling 180 of the second portion 178. FIG. 5B is a top view of an example of a portion of the primary quick-connect coupling 162 during engagement of the at least one articulation wire coupling 166 of the first portion 164 and the at least one articulation wire coupling 180 of the second portion 178. FIG. 5C is a perspective view of an example of a portion of the primary quick-connect coupling 162 after engagement of the at least one articulation wire coupling 166 of the first portion 164 and the at least one articulation wire coupling 180 of the second portion 178.

In the example shown in FIGS. 5A-5C, the at least one articulation wire coupling 166 can include a protrusion, and the at least one articulation wire coupling 180 can include a groove. The protrusion of the at least one articulation wire coupling 166 and the groove of the at least one articulation wire coupling 180 can be complementary such that the at least one articulation wire coupling 166 and the at least one articulation wire coupling 180 can be coupled together when the first portion 164 of the primary quick-connect coupling 162 and the second portion 178 of the primary quick-connect coupling 162 are coupled together. In another example, the at least one articulation wire coupling 166 can have a dovetail and the at least one articulation wire coupling 180 can include a groove. In yet another example, the at least one articulation wire coupling 166 and the at least one articulation wire coupling 180 can include any type of complementary connections that allow the at least one articulation wire coupling 166 and the at least one articulation wire coupling 180 to be removably coupled.

Figure 6:
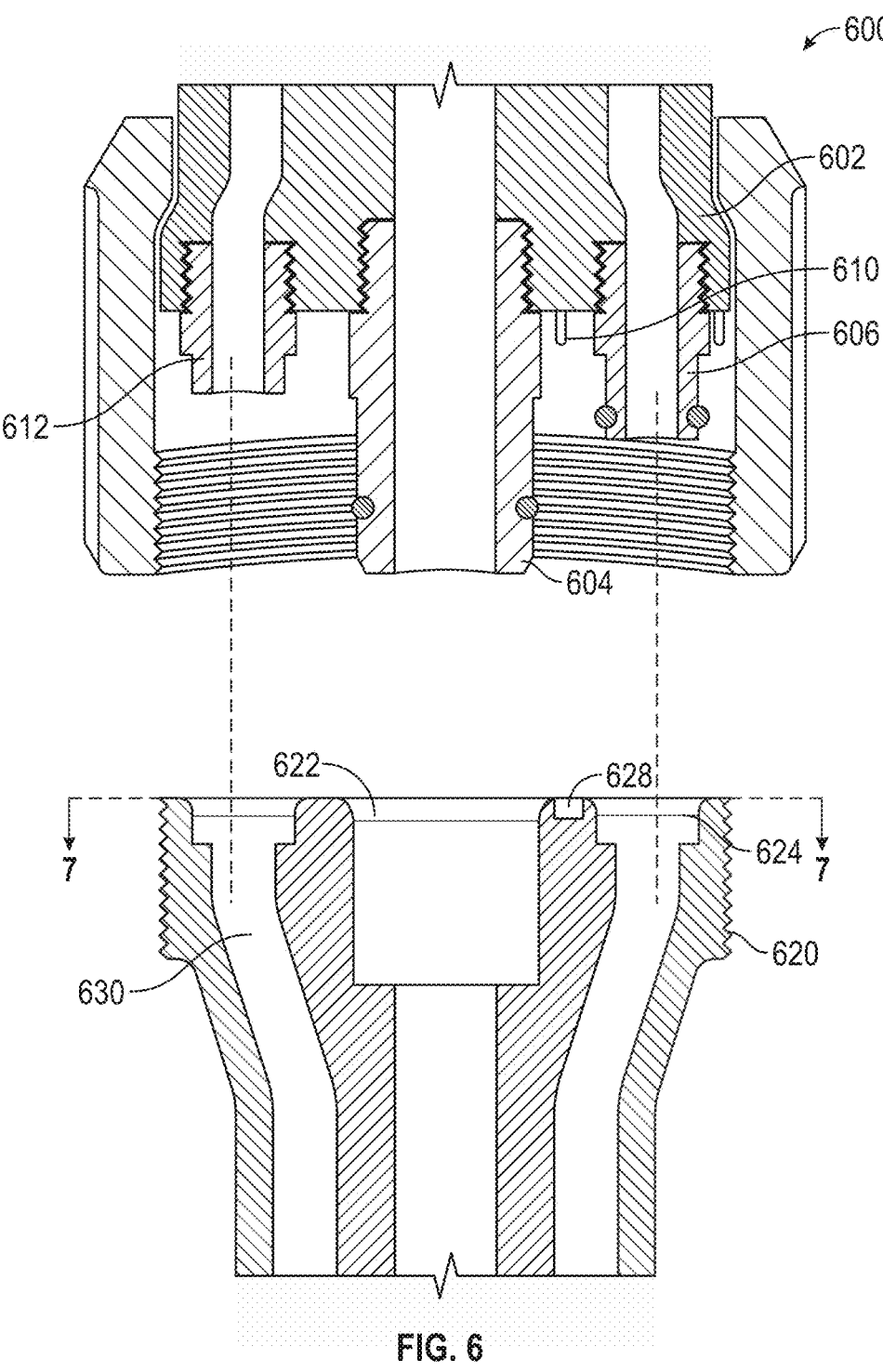
FIG. 6 is another example of a quick-connect coupling, in accordance with at least one example of the present disclosure.
Figure 7:
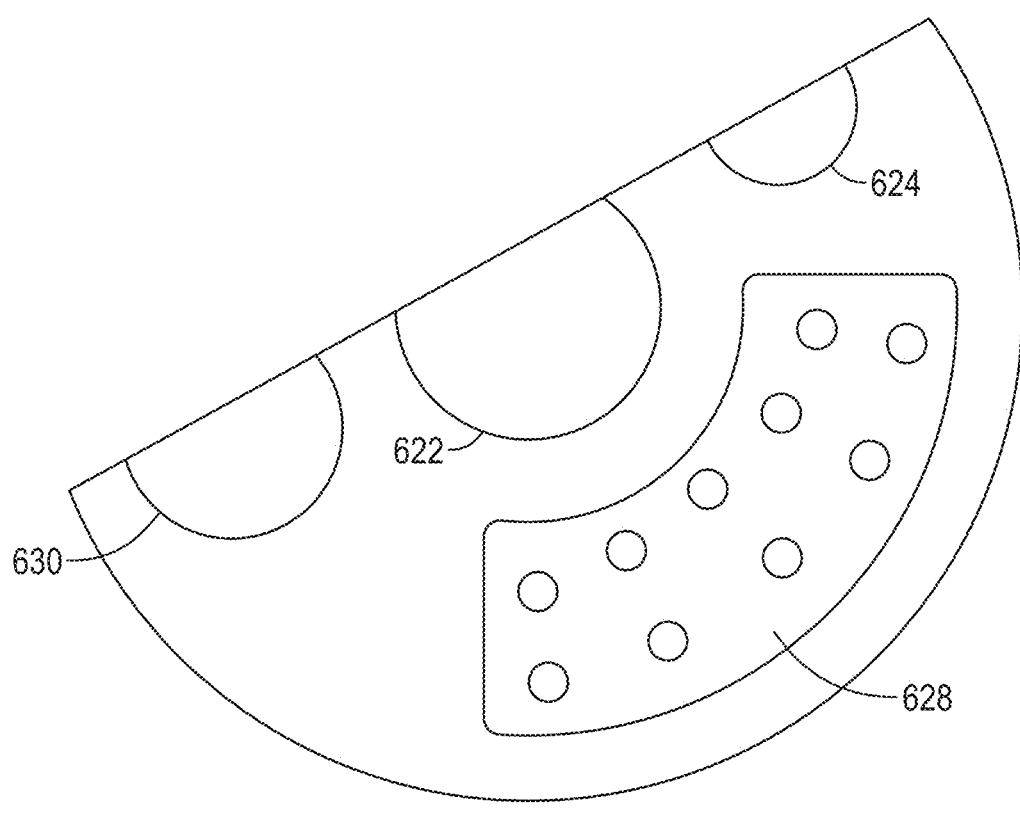
FIG. 7 is a cross-sectional view of the quick-connect coupling in FIG. 6 taken along line 7-7 showing the second portion of the quick-connect coupling, in accordance with at least one example of the present disclosure.

FIGS. 6 and 7 will be discussed together below. FIG. 6 is a cross-sectional view of another example of an auxiliary quick-connect coupling 600. FIG. 7 is a cross-sectional view of the auxiliary quick-connect coupling 600 FIG. 6 taken along line 7-7 showing the second portion 620 of the auxiliary quick-connect coupling 600.

The auxiliary quick-connect coupling 600 can be connected between a light source module and an umbilical cord of an endoscope. For example, the auxiliary quick-connect coupling 600 can be the first auxiliary quick-connect coupling 114. The auxiliary quick-connect coupling 600 can be connected between a light source module and a control head of an endoscope. For example, the auxiliary quick-connect coupling 600 can be the second auxiliary quick-connect coupling 132. The auxiliary quick-connect coupling 600 can include a first portion 602 and a second portion 620.

In a first example of the first portion 602, for example when the auxiliary quick-connect coupling 600 is the first auxiliary quick-connect coupling 114, the first portion 602 can be configured to fluidically, electrically, and optically connect the light source module to the second portion 620 of the auxiliary quick-connect coupling 600. The first portion 602 can be coupled to the light source module. For example, the first portion 602 can be integral the light source module. In another example, the first portion 602 can be removably coupled to the light source module.

In a second example of the first portion 602, for example when the auxiliary quick-connect coupling 600 is second auxiliary quick-connect coupling 132, the first portion 602 can be configured to fluidically, electrically, and optically connect the umbilical cord to the second portion 620 of the auxiliary quick-connect coupling 600. The first portion 602 can be connected to the umbilical cord. For example, the first portion 602 can be integral the umbilical cord. In another example, the first portion 602 can be removably coupled to the umbilical cord.

In each of the first and second examples, the first portion 602 can include a suction line fitting 604, a fluid-line fitting 606, at least one spring loaded pins 610, and at least one light fiber outlet 612.

The suction line fitting 604 can be integral the first portion 602 of the auxiliary quick-connect coupling 600. In another example, the suction line fitting 604 can be removably attached to the first portion 602 of the auxiliary quick-connect coupling 600. In an example, of the first example of the auxiliary quick-connect coupling 600 the first portion 602 of the auxiliary quick-connect coupling 600 and the suction line fitting 604 can be integral the light source module and one or more suction line of the light source module, respectively. In an example, of the second example of the auxiliary quick-connect coupling 600 the first portion 602 of the auxiliary quick-connect coupling 600 and the suction line fitting 604 can be integral the umbilical cord and the suction line of the umbilical cord, respectively.

In the first example of the first portion 602, the suction line fitting 604 can be configured to fluidically connect the one or more suction lines of the light source module and the second portion 620. More specifically, the suction line fitting 604 can be configured to fluidically connect the one or more suction line of the light source module to a suction line receptacle 622 of the second portion 620.

In the second example of the first portion 602, the suction line fitting 604 can be configured to fluidically connect a suction line of the umbilical cord 120 to the second portion 620. More specifically, the suction line fitting 604 can fluidically connect the suction line of the umbilical cord and the suction line receptacle 622 of the second portion 620. The suction line fitting 604 can include an O-ring to help fluidically seal the suction line fitting 604 when coupled with the suction line receptacle 622 of the second portion 620. The suction line fitting 604 can be concentric a center of the first portion 602 of the auxiliary quick-connect coupling 600.

In the first example of the first portion 602, the fluid-line fitting 606 can be configured to fluidically connect one or more fluid lines of the light source module and the second portion 620. More specifically, the fluid-line fitting 606 can be configured to fluidically connect the one or more fluid lines of the light source module and a fluid-line receptacle 624 of the second portion 620.

In the second example of the first portion 602, the fluid-line fitting 606 can be configured to fluidically connect the fluid channel 126 of the umbilical cord 120 to the second portion 620. More specifically, the fluid-line fitting 606 can be configured to fluidically connect the fluid channel 126 to the fluid-line receptacle 624 of the second portion 620. The fluid-line fitting 606 can have an O-ring to help fluidically seal the fluid-line fitting 606 when coupled with the fluid-line receptacle 624 of the second portion 620.

In the first example of the first portion 602, the at least one spring-loaded pins 610 can be configured to electrically connect the one or more electrical lines 108 of the light source module and the second portion 620. More specifically, the at least one spring-loaded pins 610 can be configured to electrically connect the one or more electrical lines 108 and an at least one closed-circuit-voltage connection pad 628 of the second portion 620.

In the second example of the first portion 602, the at least one spring-loaded pins 610 can be configured to electrically connect at least one electrical line of the umbilical cord and the second portion 620. More specifically, the at least one spring-loaded pins 610 can be configured to electrically connect the at least one spring-loaded pins 610 and the at least one closed-circuit-voltage connection pad 628 of the second portion 620.

In the first example of the first portion 602, the at least one light fiber outlet 612 can be configured to optically connect one or more light guide fiber of the light source module and the second portion 620. More specifically, the at least one light fiber outlet 612 can be configured to optically connect the one or more light guide fiber of the light source module to at least one light fiber inlet 630 of the second portion 620.

In the second example of the first portion 602, the at least one light fiber outlet 612 can be configured to optically connect one or more light guide fibers of the umbilical cord to the second portion 620. More specifically, the at least one light fiber outlet 612 can be configured to optically connect one or more light guide fibers of the umbilical cord to the at least one light fiber inlet 630 of the second portion 620.

In a first example of the second portion 620, for example when the auxiliary quick-connect coupling 600 is the first auxiliary quick-connect coupling 114, the second portion 620 can be configured to fluidically, electrically, and optically connect the first portion 602 and the umbilical cord. The second portion 620 can be coupled to the umbilical cord. For example, the second portion 620 can be integral the umbilical cord. In another example, the second portion 620 can be removably coupled the umbilical cord.

In a second example of the second portion 620, for example when the auxiliary quick-connect coupling 600 is the second auxiliary quick-connect coupling 132, the second portion 620 can be configured to fluidically, electrically, and optically connect the light source module and the control head. The second portion 620 can be coupled to the control head. For example, the second portion 620 can be integral the control head. In another example, the second portion 620 can be removably coupled the control head.

In each of the first and second examples of the second portion 620, the second portion 620 can include the suction line receptacle 622, the fluid-line receptacle 624, the at least one closed-circuit-voltage connection pad 628, and the at least one light fiber inlet 630.

The suction line receptacle 622 can be configured to receive the suction line fitting 604 of the first portion 602. The suction line receptacle 622 can be integral the second portion 620. In another example, the suction line receptacle 622 can be removably coupled to the second portion 620.

In the first example of the second portion 620, the suction line receptacle 622 can be configured to fluidically connect the suction line fitting 604 of the first portion 602 and the suction channel of the umbilical cord. More specifically, when the first portion 602 and the second portion 620 are coupled together, the suction line fitting 604 and the suction line receptacle 622 can fluidically connect the suction channel of the light source module and the suction channel of the umbilical cord.

In the second example of the second portion 620, the suction line receptacle 622 can be configured to fluidically connect the suction line fitting 604 of the first portion 602 and a suction channel of the control head. More specifically, when the first portion 602 and the second portion 620 of the auxiliary quick-connect coupling 600 are coupled together, the suction line fitting 604 and the suction line receptacle 622 can fluidically connect the suction channel of the umbilical cord and the suction channel of the control head.

In the first example of the second portion 620, the fluid-line receptacle 624 can be configured to fluidically connect the fluid-line fitting 606 to a fluid channel in the umbilical cord. More specifically, when the first portion 602 and the second portion 620 are coupled together, the fluid-line fitting 606 and the fluid-line receptacle 624 can fluidically connect the one or more fluid channels in the light source module and the fluid channel of the umbilical cord.

In the second example of the second portion 620, the fluid-line receptacle 624 can be configured to fluidically connect the fluid-line fitting 606 to at least one fluid channel of the control head. More specifically, when the first portion 602 and the second portion 620 of the auxiliary quick-connect coupling 600 are coupled together, the fluid-line fitting 606 and the fluid-line receptacle 624 can fluidically connect the fluid channel of the umbilical cord and the at least one fluid line of the control head.

In the first example of the second portion 620, the at least one closed-circuit-voltage connection pad 628 can be configured to electrically connect the at least one spring-loaded pins 610 to one or more electrical lines in the umbilical cord. More specifically, when the first portion 602 and the second portion second portion 620 are coupled together, the at least one spring-loaded pins 610 and the at least one closed-circuit-voltage connection pad 628 can electrically connect the one or more electrical lines in the light source module to the one or more electrical lines in the umbilical cord.

In the second example of the second portion 620, the at least one closed-circuit-voltage connection pad 628 can be configured to electrically connect the at least one spring-loaded pins 610 to one or more electrical lines in the control head. More specifically, when the first portion 602 and the second portion 620 are coupled together, the at least one spring-loaded pins 610 and the at least one closed-circuit-voltage connection pad 628 can electrically connect the one or more electrical lines in the umbilical cord to the one or more electrical lines in the control head.

In the first example of the second portion 620, the at least one light fiber inlet 630 can be configured to optically connect at least one light fiber outlet 612 and one or more light guide fibers in the umbilical cord. More specifically, when the first portion 602 and the second portion 620 are coupled together, the at least one light fiber outlet 612 and the at least one light fiber inlet 630 together optically connect the one or more light guide fibers in the light source module to one or more light guide fibers in the control module.

In the second example of the second portion 620, the at least one light fiber inlet 630 can be configured to optically connect the at least one light fiber outlet 612 and one or more light guide fibers in the control head. More specifically, when the first portion 602 and the second portion 620 are coupled together, the at least one light fiber outlet 612 and the at least one light fiber inlet 630 together optically connect the one or more light guide fibers in the umbilical cord to one or more light guide fibers in the control head.

As shown in FIG. 6, the first portion 602 and the suction line fitting 604 can be coupled by pressing together the first portion 602 and the suction line fitting 604 such that the suction line fitting 604, the fluid-line fitting 606, the at least one spring-loaded pins 610, and the at least one light fiber outlet 612 are coupled with the suction line receptacle 622, the fluid-line receptacle 624, the at least one closed-circuit-voltage connection pad 628, and the at least one light fiber inlet 630, respectively. The auxiliary quick-connect coupling 600 can include one or more threaded collars that engage with either the first portion 602 or the second portion 620 to help hold the first portion 602 and the second portion 620 in a coupled position. In another example, the auxiliary quick-connect coupling 600 can include a latch, or any other mechanism that can hold the first portion 602 and the second portion 620 together.

The quick-connect couplings, for example, the first auxiliary quick-connect coupling 114, second auxiliary quick-connect coupling 132, the primary quick-connect coupling 162, auxiliary quick-connect coupling 600 are solely examples of the quick-connect couplings that can be used to help with the reprocessing and re-manufacturing of the endoscope 100. Each of the first auxiliary quick-connect coupling 114, second auxiliary quick-connect coupling 132, the primary quick-connect coupling 162, auxiliary quick-connect coupling 600 can be used to make a modular endoscope that helps reduce medical waste.

Moreover, the umbilical cords and the insertion tubes, for example, the umbilical cord 120 and the insertion tube 198, can be simplified to reduce the medical waste generated by their disposal. For example, the example of the insertion tube 198 shown in FIG. 2A can also be implemented on an umbilical cord to reduce the waste of disposing of the umbilical cords used in endoscopic procedures.

Figure 8:
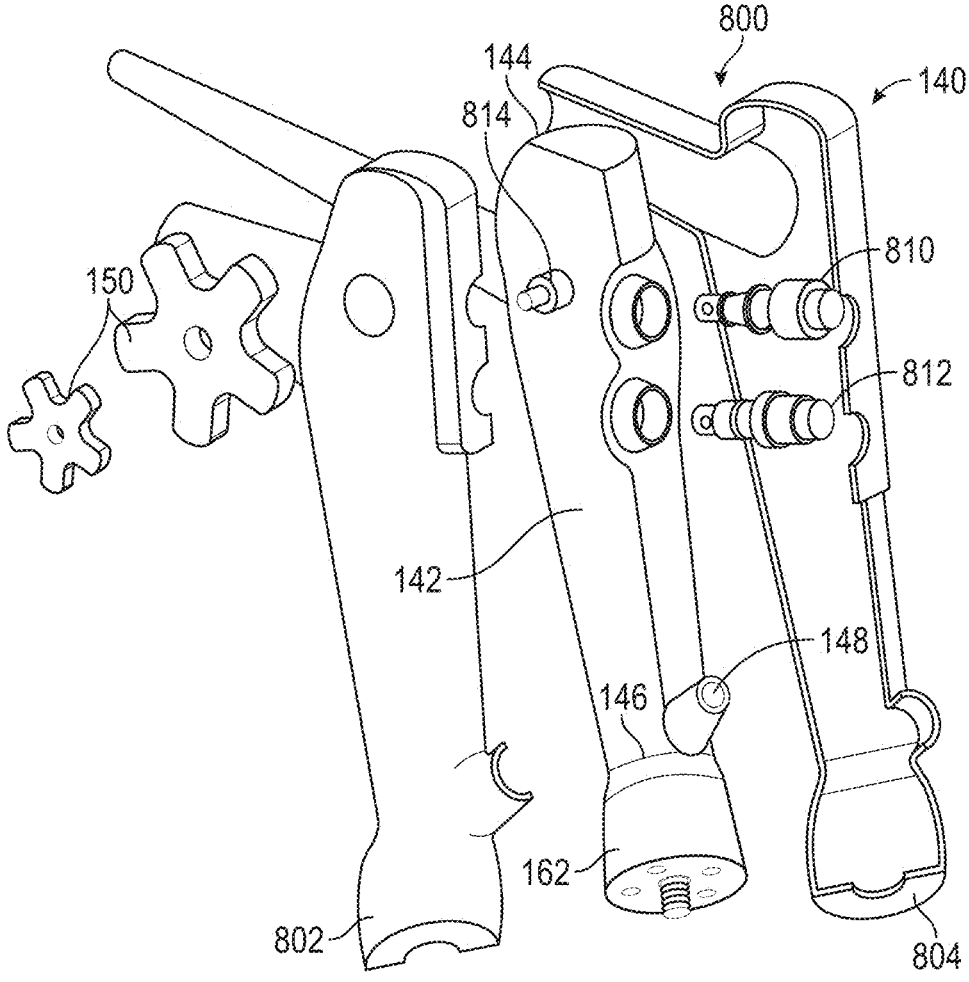
FIG. 8 is an exploded view of a control head, in accordance with at least one example of the present disclosure.

FIG. 8 is an exploded view of a control head, in accordance with at least one example of the present disclosure. The control head, for example, the control head 140, can include a clamshell 800 that surrounds the control heads and disassembles for easier cleaning of the control head 140. The clamshell 800 can include a first portion 802 and a second portion 804. The first portion 802 and the second portion 804 can come together to form the clamshell 800 around the control head.

The control head can also include a suction valve 810 configured to connect to a suction channel of the control head and suck debris from within the suction channel of the control head. The suction valve 810 can extend through the clamshell 800 such that the first portion 802 and the second portion 804 come together around the suction valve 810.

The control head can also include one or more fluid valves 812 configured to supply fluid to one or more of the fluid channels of the control head. The one or more fluid valves 812 can supply air, water, saline, or any other fluid used by an endoscope to the one or more fluid channels of the control head.

The suction valve 810 and the one or more fluid valves 812 can be removably attached to the control head. For example, the suction valve 810 and the one or more fluid valves 812 can be screwed into or removably coupled to the control head by any other means used in endoscopic technology.

The control head can include one or more control couplings 814 that extend from the control head and connect to the at least one control knobs. The one or more control couplings 814 extend from the body such that the first portion 802 and the second portion 804 can surround the one or more control couplings 814 and form the clamshell 800. The one or more control couplings 814 transfer any torque applied to the control knobs from the operators to the at least one wire within the control head. The one or more control couplings 814 extend away from the control head far enough to prevent clearance issues between the clamshell 800 and the at least one control knob.

Each of the first portion 802, the second portion 804, the suction valve 810, the one or more fluid valves 812, the one or more control couplings 814 help create a modular control head that can more easily be disassembled and prepared for reuse, recycling, cleaning, or remanufacturing.

Figure 9:
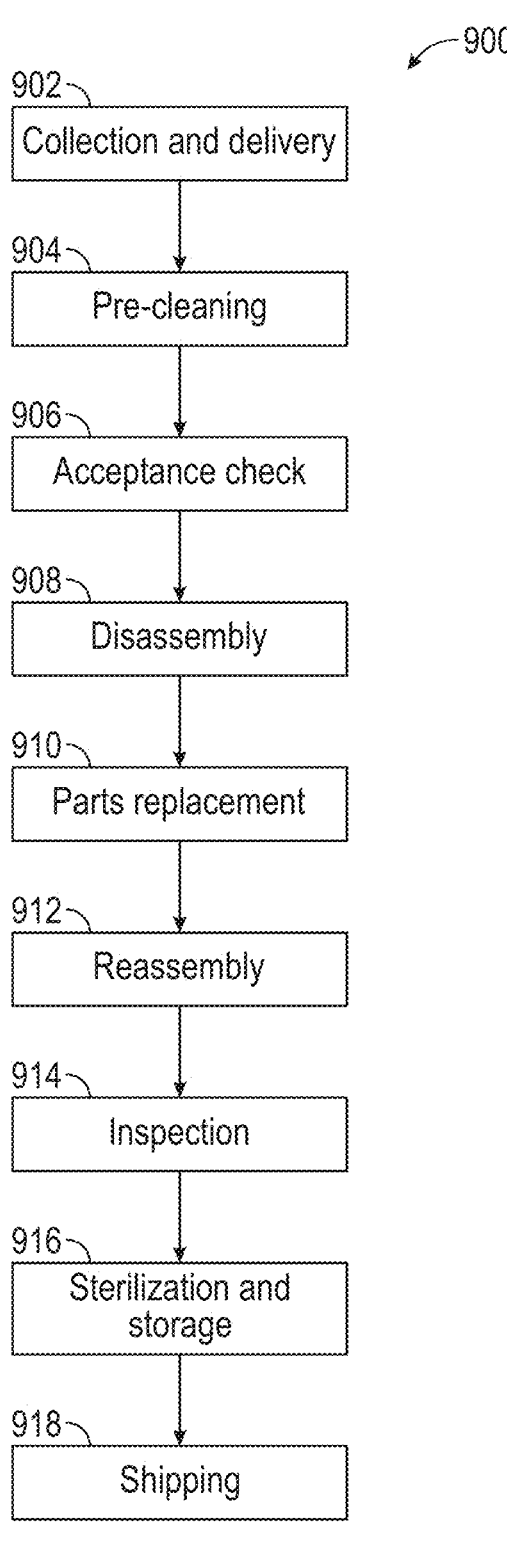
FIG. 9 is a flowchart of a method of preparing an endoscope for recycling, in accordance with at least one example of the present disclosure.

FIG. 9 illustrates a schematic view of the method 900, in accordance with at least one example of this disclosure. The method 900 can be a method of preparing and endoscope for recycling. More specific examples of the method 900 are discussed below. The steps or operations of the method 900 are illustrated in a particular order for convenience and clarity; many of the discussed operations can be performed in a different sequence or in parallel without materially impacting other operations. The method 900 as discussed includes operations performed by multiple different actors, devices, and/or systems. It is understood that subsets of the operations discussed in the method 900 can be attributable to a single actor, device, or system could be considered a separate standalone process or method.

For example, the method 900 can be the reprocessing method of an endoscope (e.g., the endoscope 100). Next, the reprocessing method for the above-described endoscope will be described. FIG. 9 is a flowchart indicating the reprocessing method of the endoscope. The endoscope described above can be disposed of after one use or can be repeatedly used a plurality of times. In the case of a configuration that is repeatedly used a plurality of times, for example, reprocessing method shown in FIG. 9 can be required.

At step 902, an operator who remanufactures collects the used endoscope 100 after it has been used for treatment and transports it to a factory or the like. The used endoscope is transported in a dedicated container to prevent contamination from the treatment of the endoscope.

At step 904, the operator cleans and sterilizes the collected and transported used endoscope. Specifically, in cleaning the endoscope, deposits adhering to insertion tube, the umbilical cord, or any of the modular components of the control head (as discussed with reference to FIG. 8) are removed by using a brush or the like. After that, to remove pathogenic microorganisms and the like derived from blood, body fluid, etc., the endoscope is cleaned with any cleaning solution of isopropanol-containing cleaning agent, proteolytic enzyme detergent, and alcohol. Thus, the endoscope is cleaned. The cleaning liquid is not limited to the cleaning liquid described above, and other cleaning liquids can be used. Further, in the sterilization of the endoscope, to sterilize the pathogenic microorganisms and the like adhering to the any other part of the endoscope, any of high-pressure steam sterilization, ethylene oxide gas sterilization, gamma ray sterilization, hydrogen peroxide and hydrogen peroxide low temperature sterilization is used. The endoscope as discussed above is modular with quick-connect couplings connecting multiple sub-assemblies, which makes the disassembly, cleaning, and sterilization easier than standard endoscopes.

At step 906, an operator performs an acceptance check of the used endoscope. In detail, the operator checks whether the used endoscope has significant defects, or the used endoscope exceeds a maximum number of reprocessing cycles.

At step 908, an operator disassembles the used endoscope. Specifically, the operator removes the insertion tube from the control head by twisting a threaded collar, rotating a first and second portion of a primary quick-connect coupling and pulling apart the first and second portion of the primary quick-connect coupling. The operator can also remove the light source module and from the control head by rotating the threaded collar and pulling a first and second portion of an auxiliary quick-connect coupling apart. The operator can also disconnect the umbilical cord from the control head by rotating the threaded collar and pulling a first and second portions of an auxiliary quick-connect coupling apart. The operator can disassemble the control head by removing each of the suction valves, the one or more fluid valves, the one or more control knobs from the one or more control couplings, and separating the first and second portions of the clamshell from one another. Therefore, the endoscope can be completely disassembled for reprocessing.

In some examples, each subassembly such as the light source module, the umbilical cord, the control head, the insertion tube, and the clamshell can have a number to indicate an order of disassembly process. The subassemblies can have a number to indicate an order of assembly process.

At step 910, an operator can replace any damaged, expired, or non-reusable components of the endoscope. For example, the operator can replace the umbilical cord and the insertion tube. As discussed above, the umbilical cord and the insertion tubes can be made less expensively and of less material, thus, the umbilical cords and insertion tubes described herein decrease the medical waste. Each of the umbilical cord and the insertion tube are equipped with quick-connect couplings. Therefore, there is advantage that it is easy to remove and replace the umbilical cord and insertion tubes on the endoscope.

In some examples, the replaced parts such as the umbilical cord, the insertion tube, and the clamshell can have a structure to be broken in step 908. This makes it possible to prevent a reuse of the replaced parts that should be discarded.

In some examples, each component of the replaced parts such as the umbilical cord, the insertion tubes, and the clamshell can include an identifier to indicate a material of the components of the replaced parts. An identifiable mark can be on a surface of the components. A color of the components may be different depending on a resin material. These identifiers can make it easy to sort the components based on the material in recycling process of the replaced parts. An operator can classify and collect the components made of the same material.

At step 912, an operator can assemble a new endoscope. In detail, the new endoscope can be assembled by connecting a light source module to an umbilical cord at a first auxiliary quick-connect coupling, connecting the umbilical cord and the control head at a second auxiliary quick-connect coupling, and connecting the control head and the insertion tube with the primary quick-connect coupling. Further, the first and second portions of the clamshell can be assembled around the control head, and the suction valve, one or more fluid valves, and control knobs can be reinstalled in the control head. Therefore, because the endoscope is modular with quick-connect couplings, the endoscope is easy to assemble in step 912.

In some examples, Step 912 can include adding an identifier to indicate the device has been modified from its original condition, such as a adding a label or other marking to designate the device as reprocessed, refurbished, or remanufactured.

At step 914, an operator can inspect and test the newly formed endoscope. Specifically, the operator can verify that the newly formed endoscope has the same effectiveness and safety as the original product by various functional tests. In examples, the operator can implement fluid, light, or electricity to the endoscope to ensure that all the connections are aligned and working as designed.

At step 916, an operator can sterilize the remanufactured endoscope and store the endoscope to reduce the endoscope's exposure to contaminants during the transportation of the endoscope. In examples, a sterilization treatment using a sterilizing gas such as ethylene oxide gas or propylene oxide gas is applied to the remanufactured endoscope, and the endoscope is stored until use.

At step 918, an operator can ship the endoscope to be used in another endoscopic procedure.

Notes and Examples

The following, non-limiting examples, detail certain aspects of the present subject matter to solve the challenges and provide the benefits discussed herein, among others.

Example 1 is an endoscope comprising: a control head including a body extending between a first end and a second end, the control head comprising: at least one control knob configured to manipulate a articulation wire; an insertion tube removably coupled to the control head, the insertion tube extending between a first end and a distal tip, the insertion tube comprising a articulation wire complementary to the articulation wire of the control head; and a quick-connect coupling configured to couple the second end of the control head and the first end of the insertion tube to enable the articulation wire of the control head and the articulation wire of the insertion tube to mechanically communicate therethrough such that moving the at least one control knob of the control head manipulates the articulation wire of the control head and the articulation wire of the insertion tube.

In Example 2, the subject matter of Example 1 optionally includes wherein the control head further comprises: a suction channel extending within the body from the first end to the second end; a light guide fiber extending within the body from the first end to the second end; and at least one fluid channel extending within the body from the first end to the second end.

In Example 3, the subject matter of any one or more of Examples 1-2 optionally include wherein the insertion tube includes an insertion tube shell comprising: a stainless-steel wire mesh extending between the first end and the distal tip of the insertion tube; a spiral metal band surrounding the stainless-steel wire mesh and extending between the first end and the distal tip of the insertion tube; and a polymer topcoat surrounding the spiral metal band and extending between the first end and the distal tip of the insertion tube, the insertion tube shell defines a lumen extending from the first end of the insertion tube to the distal tip of the insertion tube.

In Example 4, the subject matter of Example 3 optionally includes wherein the insertion tube includes: a suction channel extending within the lumen from the first end to the distal tip; a light guide fiber extending within the lumen from the first end and through the distal tip; and at least one fluid channel extending within the lumen from the first end and through the distal tip.

In Example 5, the subject matter of Example 4 optionally includes wherein a first portion of the quick-connect coupling is formed on the second end of the control head and a second portion of the quick-connect coupling is formed on the first end of the insertion tube.

In Example 6, the subject matter of Example 5 optionally includes wherein the first portion of the quick-connect coupling comprises: a suction line fitting surrounding the suction channel and having an O-ring surrounding the suction line fitting; at least one articulation wire coupling attached to the articulation wire within the control head; at least one fluid line outlet fluidically connected to the at least one fluid channel of the control head; a light guide fiber outlet in optical communication with the light guide fiber of the control head, the light guide fiber outlet having a centerline; and at least two twist-lock grooves.

In Example 7, the subject matter of Example 6 optionally includes wherein the first portion of the quick-connect coupling is circular having a center point, the suction line fitting is concentrically centered on the center point of the quick-connect coupling such that the first portion of the quick-connect coupling is configured to rotate about the suction line fitting.

In Example 8, the subject matter of Example 7 optionally includes wherein the first portion of the quick-connect coupling is includes a first diameter, the at least one fluid line outlet and the light guide fiber outlet are spaced around the center point at the first diameter.

In Example 9, the subject matter of Example 8 optionally includes wherein the first portion of the quick-connect coupling includes a second diameter, the at least one articulation wire coupling is spaced around the center point at the second diameter.

In Example 10, the subject matter of Example 9 optionally includes wherein the first portion of the quick-connect coupling includes a third diameter, the at least two twist-lock grooves are spaced around the center point at the third diameter.

In Example 11, the subject matter of any one or more of Examples 6-10 optionally include wherein the second portion of the quick-connect coupling comprises: a suction line receptacle configured to receive the suction line fitting of the first portion of the quick-connect coupling; at least one articulation wire coupling attached to the at least one articulation wire within the insertion tube; at least one fluid line inlet fluidically connected to the at least one fluid line of the insertion tube; and a light guide fiber inlet optically connected to the light guide fiber of the insertion tube.

In Example 12, the subject matter of Example 11 optionally includes wherein the second portion of the quick-connect coupling further comprises: at least two twist-lock protrusions configured to be inserted in the at least two twist-lock grooves of the first portion of the quick-connect coupling and configured to stop rotation of the first portion of the quick-connect coupling when the first portion of the quick-connect coupling and the second portion of the quick-connect coupling are properly aligned.

In Example 13, the subject matter of Example 12 optionally includes wherein the second portion of the quick-connect coupling is circular having a center point, the suction line receptacle is concentrically centered on the center point of the quick-connect coupling to align with the suction line fitting when the first portion of the quick-connect coupling is coupled to the second portion of the quick-connect coupling.

In Example 14, the subject matter of any one or more of Examples 12-13 optionally include wherein the second portion of the quick-connect coupling is circular having a center point and a first diameter, the at least one fluid inlet and the at least one light guide fiber inlet are spaced around the center point at the first diameter so that the at least one fluid inlet and the light guide fiber inlet align with the at least one fluid outlet and the light guide fiber outlet of the first portion of the quick-connect coupling when the first portion of the quick-connect coupling is coupled to the second portion of the quick-connect coupling.

In Example 15, the subject matter of Example 14 optionally includes wherein the second portion of the quick-connect coupling is circular having a second diameter, the at least one articulation wire coupling are spaced around the center point at the second diameter so that the at least one articulation wire coupling is aligned with the at least one articulation wire coupling of the first portion of the quick-connect coupling when the first portion of the quick-connect coupling is coupled to the second portion of the quick-connect coupling.

In Example 16, the subject matter of Example 15 optionally includes wherein the second portion of the quick-connect coupling is circular having a third diameter, the at least two twist-lock protrusions are spaced around the center point at the third diameter so that the at least two twist-lock protrusions align with the at least two twist-lock grooves of the first portion of the quick-connect coupling when the first portion of the quick-connect coupling is coupled to the second portion of the quick-connect coupling.

In Example 17, the subject matter of any one or more of Examples 9-16 optionally include wherein the quick-connect coupling further comprises a threaded collar, and wherein the second portion of the quick-connect coupling further comprises a threaded surface formed on an outer periphery of the second portion of the quick-connect coupling, wherein threaded collar and the threaded surface on the outer periphery of the second portion of the quick-connect coupling are complementary to one another to couple the first portion of the quick-connecting coupling and the second portion of the quick-connecting coupling.

In Example 18, the subject matter of any one or more of Examples 1-17 optionally include wherein the control head comprises: a first clamshell half; and a second clamshell half, the first clamshell half and the second clamshell half together surround the body of the control head, the first clamshell half and the second clamshell have a plurality of apertures to enable the control head to be connected to an umbilical cord, an insertion tube, an air source, a suction source, and a water source.

In Example 19, the subject matter of any one or more of Examples 1-18 optionally include a light source module comprising: a suction channel configured to provide suction to the endoscope to remove excess water or debris from in front of the distal tip of the insertion tube; a light guide fiber configured to provide light at the distal tip of the insertion tube; and a first connection component configured to permit the suction channel and the light guide fiber to pass therethrough.

In Example 20, the subject matter of Example 19 optionally includes an umbilical cord extending between a first end and a second end, the umbilical cord comprising: a suction channel extending from the first end to the second end; a light guide fiber extending from the first end to the second end; and a second connection component on the first end of the umbilical cord configured to be coupled to the first connection component of the light source module and configured to permit the suction channel, and the light guide fiber to pass therethrough.

In Example 21, the subject matter of Example 20 optionally includes the umbilical cord further comprising: a third connection component on the second end of the umbilical cord configured to be coupled to the first end of the control head and to permit the suction channel and the light guide fiber to pass therethrough.

In Example 22, the subject matter of any one or more of Examples 20-21 optionally include the first connection component further comprising: a suction-line fitting surrounding the suction channel of the light source module; a light guide fiber fitting surrounding the light guide fiber of the light source module; and at least one spring-loaded pin configured to transmit electrical current from the light source module to the control head.

In Example 23, the subject matter of Example 22 optionally includes wherein the suction-line fitting comprises an O-ring.

In Example 24, the subject matter of any one or more of Examples 22-23 optionally include the second connection component further comprising: a suction-line receptacle configured to receive the suction-line fitting to fluidically connect the suction channel of the light source module and the suction channel of the umbilical cord; a light guide fiber receptacle configured to receive the light guide fiber fitting to fluidically connect the light guide fiber of the light source module to the light guide fiber of the umbilical cord; and at least one closed-circuit-voltage connection pad configured to contact the at least one spring-loaded pin to transmit electrical current from the light source module into the umbilical cord.

In Example 25, the subject matter of Example 24 optionally includes wherein an outer body of the second connection component comprises a threaded surface are configured to receive a threaded-collar that encloses the first connection component, the thread on the threaded-collar are complementary to the threaded surface of the outer body of the second connection component so that the thread on the threaded-collar and the threaded surface of the outer body can couple the first connection component and the second connection component.

In Example 26, the subject matter of Example 25 optionally includes the umbilical cord, the insertion tube, and the clamshell include an identifier to indicate a material, the method comprising: classifying components of the umbilical cord, the insertion tube, and the clamshell on the identifier, and packaging classified components for recycling.

Example 27 is an assembly comprising: a first component having at least one drainage channel and at least one fluid channel; a second component having at least one drainage channel and at least one fluid channel; and a quick-connect coupling configured to: couple the first component to the second component; fluidically connect the at least one drainage channel of the first component to the at least one drainage channel of the second component; and fluidically connect the at least one fluid channel of the first component to the at least one fluid channel of the second component.

In Example 28, the subject matter of Example 27 optionally includes wherein the quick-connect coupling comprises a first portion attached to the first component and a second portion connected to the second component.

In Example 29, the subject matter of Example 28 optionally includes wherein the first portion of the quick-connect coupling comprises: at least one drainage channel fitting surrounding each of the at least one drainage channel of the first component; at least one fluid outlet fluidically connected to each of the at least one fluid channels of the first component; and at least one twist-lock connection groove formed in the first portion of the quick-connect coupling.

In Example 30, the subject matter of Example 29 optionally includes wherein the second portion of the quick-connect coupling comprises: at least one drainage channel receptacle configured to receive the at least one drainage fitting and fluidically connected to the drainage channel of the second component; at least one fluid inlet fluidically connected to each of the at least one fluid channels of the second component; and at least one twist-lock connection protrusion configured to engage with the at least one twist-lock connection groove of the first portion of the quick-connect coupling when the first portion and the second portion of the quick-connect coupling are coupled together.

Example 31 is a method for reprocessing an instrument for surgery, the instrument having a control head with a body extending between a first end and a second end, the control head having an articulation wire extending from a control knob and through the body to the second end of the control head, an insertion tube removably coupled to the control head, the insertion tube including an articulation wire complementary to the articulation wire of the control head, a quick-connect coupling configured to couple the second end of the control head to the first end of the insertion tube, and to enable the articulation wire of the control head and the articulation wire of the insertion tube to mechanically communicate therethrough such that moving the control knob of the control head manipulates the articulation wire of the control head and the articulation wire of the insertion tube the method comprising: obtaining the instrument; preparing the articulation wire for decoupling by setting the control knob on the control head to a zero position; disconnecting the control head from the insertion tube by decoupling the quick-connect coupling; removing the control knobs and preparing the control knobs for recycling; sanitizing the control head; and storing the control head in a sterile container.

In one or more examples, when the control knob on the control head is set to a zero position, the insertion tube is not articulated and the common planes of the articulating wire couplings are aligned so the articulating wire couplings can be coupled or decoupled.

In Example 32, the subject matter of Example 31 optionally includes the instrument further including a light source module having a plurality of channels therethrough and a first connection component, an umbilical cord including a plurality of channels therethrough and a second and third connection component, the first connection component and the second connection component are configured to couple the light source module to the umbilical cord, and the third connection component is configured to connect the umbilical cord to the control head, the method further comprising: disconnecting the light source module from the umbilical cord by decoupling the first connection component and the second connection component; disconnecting the umbilical cord from the control head by decoupling the third connection component; preparing the umbilical cord for disposal; sanitizing the light source module; and packaging the light source module in a sanitized container for later use.

In Example 33, the subject matter of Example 32 optionally includes the instrument further includes a clamshell surrounding the control head having holes to allow a suction valve, an air valve, and a water valve therethrough for connection to the control head, the method comprising: removing a clamshell surrounding the control head and preparing the clamshell for recycling; removing a suction valve, an air valve, and a water valve to reuse on future instruments; sanitizing the suction valve, the air valve, and the water valve; and packaging the suction valve, the air valve, and the water valve in a sanitized package.

In Example 34, the apparatuses or method of any one or any combination of Examples 1-33 can optionally be configured such that all elements or options recited are available to use or select from.

The above-detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An endoscope comprising:
a control head including a body extending between a first end and a second end, the control head having at least one control knob configured to manipulate an articulation wire;
an insertion tube removably coupled to the control head, the insertion tube extending between a first end and a distal tip, the insertion tube comprising an articulation wire complementary to the articulation wire of the control head, wherein the insertion tube includes an insertion tube shell comprising:
a stainless-steel wire mesh extending between the first end and the distal tip of the insertion tube;

a spiral metal band surrounding the stainless-steel wire mesh and extending between the first end and the distal tip of the insertion tube;
a polymer topcoat surrounding the spiral metal band and extending between the first end and the distal tip of the insertion tube, the insertion tube shell defines a lumen extending from the first end of the insertion tube to the distal tip of the insertion tube;
a suction channel extending within the lumen from the first end to the distal tip;
a light guide fiber extending within the lumen from the first end and through the distal tip; and
at least one fluid channel extending within the lumen from the first end and through the distal tip; and
a quick-connect coupling configured to couple the second end of the control head and the first end of the insertion tube to enable the articulation wire of the control head and the articulation wire of the insertion tube to mechanically communicate therethrough such that moving the at least one control knob of the control head manipulates the articulation wire of the control head and the articulation wire of the insertion tube, a first portion of the quick-connect coupling formed on the second end of the control head, the first portion of the quick-connect coupling including:
a suction line fitting surrounding the suction channel and having an O-ring surrounding the suction line fitting;
at least one articulation wire coupling attached to the articulation wire within the control head;
at least one fluid line outlet fluidically connected to the at least one fluid channel of the control head;
a light guide fiber outlet in optical communication with the light guide fiber of the control head, the light guide fiber outlet having a centerline; and
at least two twist-lock grooves;
wherein:
a second portion of the quick-connect coupling formed on the first end of the insertion tube;
the first portion of the quick-connect coupling is circular, having a center point, the suction line fitting is concentrically centered on the center point of the quick-connect coupling, such that the first portion of the quick-connect coupling is configured to rotate about the suction line fitting; and
the first portion of the quick-connect coupling includes a first diameter, the at least one fluid line outlet and the light guide fiber outlet are spaced around the center point at the first diameter.

2. The endoscope of claim 1, wherein the control head further comprises:
a suction channel extending within the body from the first end to the second end;
a light guide fiber extending within the body from the first end to the second end; and
at least one fluid channel extending within the body from the first end to the second end.

3. The endoscope of claim 1, wherein the first portion of the quick-connect coupling includes a second diameter, the at least one articulation wire coupling is spaced around the center point at the second diameter.

4. The endoscope of claim 3, wherein the first portion of the quick-connect coupling includes a third diameter, the at least two twist-lock grooves are spaced around the center point at the third diameter.

5. The endoscope of claim 3, wherein the quick-connect coupling further comprises a threaded collar, and wherein the second portion of the quick-connect coupling further comprises a threaded surface formed on an outer periphery of the second portion of the quick-connect coupling, wherein threaded collar and the threaded surface on the outer periphery of the second portion of the quick-connect coupling are complementary to one another to couple the first portion of the quick-connecting coupling and the second portion of the quick-connecting coupling.

6. The endoscope of claim 1, wherein the second portion of the quick-connect coupling comprises:
   a suction line receptacle configured to receive the suction line fitting of the first portion of the quick-connect coupling;
   at least one articulation wire coupling attached to the at least one articulation wire within the insertion tube;
   at least one fluid line inlet fluidically connected to the at least one fluid line of the insertion tube; and
   a light guide fiber inlet optically connected to the light guide fiber of the insertion tube.

7. The endoscope of claim 6, wherein the second portion of the quick-connect coupling further comprises:
   at least two twist-lock protrusions configured to be inserted in the at least two twist-lock grooves of the first portion of the quick-connect coupling and configured to stop rotation of the first portion of the quick-connect coupling when the first portion of the quick-connect coupling and the second portion of the quick-connect coupling are properly aligned.

8. The endoscope of claim 7, wherein the second portion of the quick-connect coupling is circular having a center point, the suction line receptacle is concentrically centered on the center point of the quick-connect coupling to align with the suction line fitting when the first portion of the quick-connect coupling is coupled to the second portion of the quick-connect coupling.

9. The endoscope of claim 7, wherein the second portion of the quick-connect coupling is circular having a center point and a first diameter, the at least one fluid inlet and the at least one light guide fiber inlet are spaced around the center point at the first diameter so that the at least one fluid inlet and the light guide fiber inlet align with the at least one fluid outlet and the light guide fiber outlet of the first portion of the quick-connect coupling when the first portion of the quick-connect coupling is coupled to the second portion of the quick-connect coupling.

10. The endoscope of claim 9, wherein the second portion of the quick-connect coupling is circular having a second diameter, the at least one articulation wire coupling are spaced around the center point at the second diameter so that the at least one articulation wire coupling is aligned with the at least one articulation wire coupling of the first portion of the quick-connect coupling when the first portion of the quick-connect coupling is coupled to the second portion of the quick-connect coupling.

11. The endoscope of claim 10, wherein the second portion of the quick-connect coupling is circular having a third diameter, the at least two twist-lock protrusions are spaced around the center point at the third diameter so that the at least two twist-lock protrusions align with the at least two twist-lock grooves of the first portion of the quick-connect coupling when the first portion of the quick-connect coupling is coupled to the second portion of the quick-connect coupling.

12. The endoscope of claim 1, wherein the control head comprises:
   a first clamshell half, and a second clamshell half, the first clamshell half and the second clamshell half together surround the body of the control head, the first clamshell half and the second clamshell have a plurality of apertures to enable the control head to be connected to an umbilical cord, an insertion tube, an air source, a suction source, and a water source.

13. An endoscope comprising:
   a control head including a body extending between a first end and a second end, the control head having at least one control knob configured to manipulate an articulation wire;
   an insertion tube removably coupled to the control head, the insertion tube extending between a first end and a distal tip, the insertion tube comprising an articulation wire complementary to the articulation wire of the control head, wherein the insertion tube includes an insertion tube shell comprising:
      a stainless-steel wire mesh extending between the first end and the distal tip of the insertion tube;
      a spiral metal band surrounding the stainless-steel wire mesh and extending between the first end and the distal tip of the insertion tube;
      a polymer topcoat surrounding the spiral metal band and extending between the first end and the distal tip of the insertion tube, the insertion tube shell defines a lumen extending from the first end of the insertion tube to the distal tip of the insertion tube;
      a suction channel extending within the lumen from the first end to the distal tip;
      a light guide fiber extending within the lumen from the first end and through the distal tip; and
      at least one fluid channel extending within the lumen from the first end and through the distal tip; and
   a quick-connect coupling configured to couple the second end of the control head and the first end of the insertion tube to enable the articulation wire of the control head and the articulation wire of the insertion tube to mechanically communicate therethrough such that moving the at least one control knob of the control head manipulates the articulation wire of the control head and the articulation wire of the insertion tube, a first portion of the quick-connect coupling is formed on the second end of the control head, wherein the first portion of the quick-connect coupling comprises:
      a suction line fitting surrounding the suction channel and having an O-ring surrounding the suction line fitting;
      at least one articulation wire coupling attached to the articulation wire within the control head;
      at least one fluid line outlet fluidically connected to the at least one fluid channel of the control head;
      a light guide fiber outlet in optical communication with the light guide fiber of the control head, the light guide fiber outlet having a centerline; and
      at least two twist-lock grooves; and
   wherein a second portion of the quick-connect coupling is formed on the first end of the insertion tube, and wherein the second portion of the quick-connect coupling comprises:
   a suction line receptacle configured to receive the suction line fitting of the first portion of the quick-connect coupling;
   at least one articulation wire coupling attached to the at least one articulation wire within the insertion tube;
   at least one fluid line inlet fluidically connected to the at least one fluid line of the insertion tube;

a light guide fiber inlet optically connected to the light guide fiber of the insertion tube; and at least two twist-lock protrusions configured to be inserted in the at least two twist-lock grooves of the first portion of the quick-connect coupling and configured to stop rotation of the first portion of the quick-connect coupling when the first portion of the quick-connect coupling and the second portion of the quick-connect coupling are properly aligned; and wherein the second portion of the quick-connect coupling is circular having a center point and a first diameter, the at least one fluid inlet and the at least one light guide fiber inlet are spaced around the center point at the first diameter so that the at least one fluid inlet and the light guide fiber inlet align with the at least one fluid outlet and the light guide fiber outlet of the first portion of the quick-connect coupling when the first portion of the quick-connect coupling is coupled to the second portion of the quick-connect coupling.

* * * * *